(12) United States Patent
Sonesson et al.

(10) Patent No.: US 11,078,158 B2
(45) Date of Patent: Aug. 3, 2021

(54) (+)-3-(2,3-DIFLUOROPHENYL)-3-METHOXYPYRROLIDINE OR PHARMACEUTICALLY ACCEPTABLE SALTS THEREOF, A PROCESS FOR PREPARATION THEREOF AND USES THEREOF

(71) Applicant: INTEGRATIVE RESEARCH LABORATORIES SWEDEN AB, Gothenburg (SE)

(72) Inventors: Clas Sonesson, Billdal (SE); Maija Buksa, Riga (LV); Inese Reine, Riga (LV)

(73) Assignee: INTEGRATIVE RESEARCH LABORATORIES SWEDEN AB, Gothenburg (SE)

( * ) Notice: Subject to any disclaimer, the term of this patent is extended or adjusted under 35 U.S.C. 154(b) by 99 days.

(21) Appl. No.: 16/338,055

(22) PCT Filed: May 18, 2018

(86) PCT No.: PCT/EP2018/063123
§ 371 (c)(1),
(2) Date: Mar. 29, 2019

(87) PCT Pub. No.: WO2018/211080
PCT Pub. Date: Nov. 22, 2018

(65) Prior Publication Data
US 2020/0024231 A1    Jan. 23, 2020

(30) Foreign Application Priority Data

May 19, 2017 (EP) .................. 17171938
Oct. 9, 2017 (EP) .................. 17195451
Dec. 14, 2017 (EP) .................. 17207406
Jan. 12, 2018 (EP) .................. 18151428

(51) Int. Cl.
*C07D 207/12* (2006.01)

(52) U.S. Cl.
CPC ........ *C07D 207/12* (2013.01); *C07B 2200/13* (2013.01)

(58) Field of Classification Search
CPC ........ C07D 207/12; C07C 57/15; C07C 57/34
See application file for complete search history.

(56) References Cited

FOREIGN PATENT DOCUMENTS

| EP | 0586229 A1 | 3/1994 |
| EP | 1582524 A1 | 10/2005 |
| WO | WO 2008148801 | * 12/2008 |
| WO | WO-2010/058018 A1 | 5/2010 |

OTHER PUBLICATIONS

Ganapathy et al., Molecular and Ligand-Binding Characterization of the S-Receptor in Jurkat Human T Lymphocyte Cell Line. J Pharmacol Exp Ther. 1999; 289:251.
Gould et al., Pyrrolidines, IX. 3-Aryl-3-pyrrolidinols. J Med Chem. 1964; 7(1):60-7.
International Search Report and Written Opinion dated Aug. 8, 2018 by the International Searching Authority for Patent Application No. PCT/EP2018/063123, which was filed on May 18, 2018 and published as WO 2018/211080 dated Nov. 22, 2018 (Inventor—Sonesson et al.; Applicant—Integrative Research Laboratories Sweden AB) (15 pages).

* cited by examiner

*Primary Examiner* — Noble E Jarrell
(74) *Attorney, Agent, or Firm* — Ballard Spahr LLP

(57) ABSTRACT

The disclosure provides a process for manufacturing thereof a salt of Formula IIb:

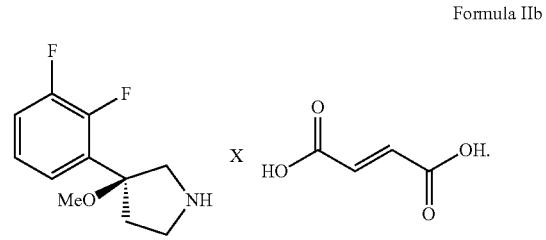

Formula IIb

14 Claims, 2 Drawing Sheets

# (+)-3-(2,3-DIFLUOROPHENYL)-3-METHOXYPYRROLIDINE OR PHARMACEUTICALLY ACCEPTABLE SALTS THEREOF, A PROCESS FOR PREPARATION THEREOF AND USES THEREOF

CROSS-REFERENCE TO RELATED APPLICATIONS

This application is a U.S. National Phase Application of International Application No. PCT/EP2018/063123, filed May 18, 2018, which claims priority to European Patent Application Nos. EP 17171938.8, filed May 19, 2017; EP 17195451.4, filed Oct. 9, 2017; EP 17207406.4, filed Dec. 14, 2017; and EP 18151428.2, filed Jan. 12, 2018, each of which are hereby incorporated by reference in their entirety.

TECHNICAL FIELD

The present disclosure concerns a process for preparing the compound (+)-3-(2,3-difluorophenyl)-3-methoxypyrrolidine, or a pharmaceutically acceptable salt thereof, in high chemical and/or enantiomeric purity. The present disclosure also concerns a combination of (−)-dibenzoyl-L-tartaric acid and 3-(2,3-difluorophenyl)-3-methoxypyrrolidine as an intermediate in the synthesis of (+)-3-(2,3-difluorophenyl)-3-methoxypyrrolidine. In particular, the present disclosure concerns a fumaric acid salt of the compound (+)-3-(2,3-difluorophenyl)-3-methoxypyrrolidine, a method for preparation thereof as well as uses thereof.

BACKGROUND

The cerebral cortex encompasses several major regions that are involved in higher functions such as thought, feelings, memory and planning. Biogenic amines, i.e. dopamine, norepinephrine and serotonin, are important for mammalian cortical function.

The ascending dopamine and norepinephrine pathways innervate the cortex. The serotonergic neurons of the CNS project to virtually all regions of the brain including the cerebral cortex. Primary or secondary dysfunctions in the activity of these pathways lead to dysregulation of the activity at dopamine and norepinephrine and serotonin receptors in these brain areas and subsequently to manifestations of psychiatric and neurological symptoms. The biogenic amines of the cortex modulate several aspects of cortical functions controlling affect, anxiety, motivation, cognition, attention, arousal and wakefulness. Thus, the catecholamines dopamine and norepinephrine exert strong influence on the prefrontal cortical areas, the integrity of which is essential for the so-called executive cognitive functions, related to e.g. attention, planning of actions and impulse control. Norepinephrine is a major part in the circuitry regulating anxiety and fear and is thus believed to be dysregulated in anxiety disorders such as panic disorders, generalized anxiety disorder (GAD) and specific phobias. Concerning mood and affective functions, the usefulness of compounds facilitating particularly norepinephrine and serotonin neurotransmission in the treatment of depression and anxiety has strongly contributed to the widely-accepted concept that these neurotransmitters are both involved in the regulation of affective functions.

In general, compounds specifically affecting the transmission of biogenic amines, more precisely monoamines, norepinephrine, dopamine and serotonin are successfully used to alleviate the affective, cognitive, or attentional symptoms in patients suffering from e.g. depression, anxiety and attention deficit hyperactivity disorders (ADHD).

Furthermore, the monoamine systems in the cortex are known to be directly or indirectly involved in the core symptoms of schizophrenia. Based on a synthesis of biochemical and genetic findings along with neuropsychological observations indicating dysfunction of specific cortical areas in schizophrenia, it has been proposed that this disorder emerges as various pathological etiologies converge upon cortical function leading to dysregulation of the cortical micro-circuitry, which is clinically manifested as the symptoms of schizophrenia. This cortical micro-circuitry is regulated by several neurotransmitters, including glutamate, GABA, and dopamine.

WO 2010/058018 discloses 3-phenyl-3-methoxy-pyrrolidine derivatives useful for modulating extracellular levels of catecholamines, dopamine and norepinephrine, in cerebral cortical areas of the mammalian brain, and more specifically for the treatment of central nervous system disorders. The compound 3-(2,3-difluorophenyl)-3-methoxypyrrolidine is disclosed in the form as a racemate, and as the corresponding (+)- and (−) enantiomers, respectively. The racemate is disclosed in its non-salt form (Preparation 19) and in the form of a hydrochloric acid salt (Example 12). The two enantiomers are disclosed in the non-salt form as well as in the form of an oxalic acid salt (Examples 5 and 7, respectively).

Further, a resolution process of the racemate of 3-(2,3-difluorophenyl)-3-methoxypyrrolidine into (+)-3-(2,3-difluorophenyl)-3-methoxypyrrolidine is disclosed in WO 2010/058018, said resolution process comprising benzylation of the pyrrolidine nitrogen followed by separation using chiral HPLC and debenzylation of the pyrrolidine nitrogen.

It is well recognized that enantiomers of chiral drugs frequently interact differently with chiral macromolecules such as receptors and/or enzymes in the human body, and therefore may exhibit differences in biological activities such as pharmacology, toxicology, and pharmacokinetics. Consequently, it is desirable to develop and launch a new drug as a single enantiomer rather than as a racemic mixture so as to fully take advantage of the pharmacodynamic and pharmacokinetic properties of the drug and/or avoid possible drawbacks associated with the racemic mixture. Further, it is desirable to have knowledge of the three-dimensional arrangement of a chiral molecule such as an enantiomer of an investigational drug in order to increase the understanding of its interaction with enzymes, receptors etc.

Further, the synthesis of drugs such as synthesis on a large scale is known to be challenging. One of the major challenges is that even small amounts of impurities may be difficult and/or costly to remove. In case of chiral drugs such as enantiomers it is necessary to find methods which allow for production of the drug in both chemical and stereochemical purity. Moreover, the drug has to be provided in a form making it suitable for handling during, for instance, storage and transportation.

The compound (+)-3-(2,3-difluorophenyl)-3-methoxypyrrolidine disclosed in WO 2010/058018 is currently in clinical development as a cortical enhancer drug for treatment of Parkinson Disease Dementia (PD-D) and Behavioral and Psychological Symptoms of Dementia (BPSD).

The previous method for the synthesis of (+)-3-(2,3-difluorophenyl)-3-methoxypyrrolidine has been intended for manufacturing of small to intermediate amounts. However, the further investigation of the compound and its development have resulted in a need for further methods enabling synthesis such as large-scale synthesis of (+)-3-(2,3-difluorophenyl)-3-methoxypyrrolidine, or a pharmaceutically acceptable salt thereof, with equivalent or improved chemical and/or stereochemical purity. Moreover, there is a need for an alternative to the oxalic acid salt of (+)-3-(2,3-difluorophenyl)-3-methoxypyrrolidine, since oxalic acid is known to be associated with kidney disorders such as kidney failure due to formation of calcium oxalate.

To increase the versatility and/or availability of (+)-3-(2, 3-difluorophenyl)-3-methoxypyrrolidine, or a pharmaceutically acceptable salt thereof, and/or enable industrial production thereof, there remains a need for alternative methods. Further, there is a need for a form of (+)-3-(2,3-difluorophenyl)-3-methoxypyrrolidine exhibiting satisfactory pharmaceutical properties as well as satisfactory handling and drug properties, in particular on an industrial scale.

It is an object of the present disclosure to provide a method fulfilling said need and/or providing a (+)-3-(2,3-difluorophenyl)-3-methoxypyrrolidin, or pharmaceutically acceptable salt thereof, exhibiting satisfactory pharmaceutical properties as well as handling and drug properties.

SUMMARY

Figure 1:
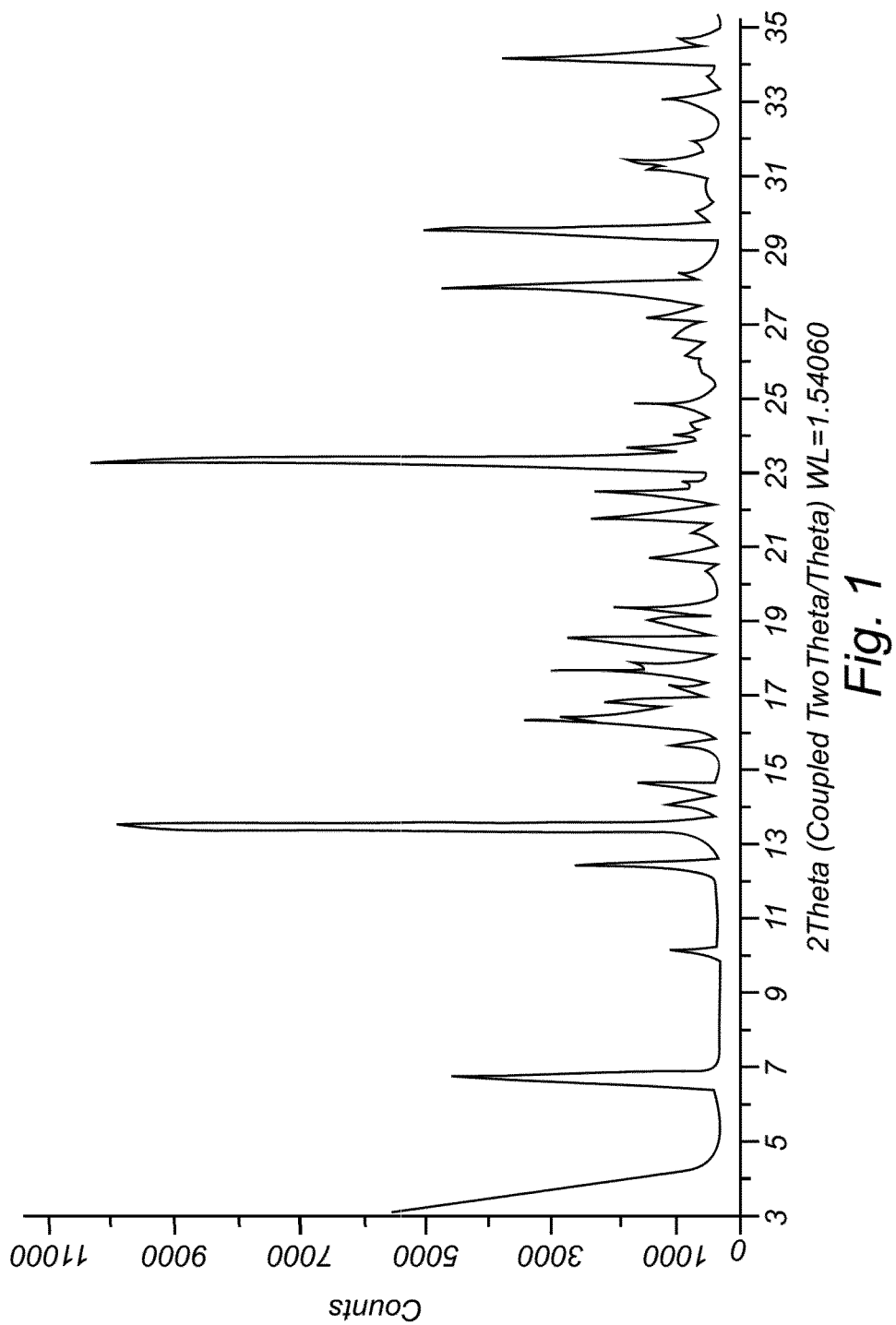
FIG. 1 shows an XRPD spectrum of the salt of Formula IIb.
Figure 2:
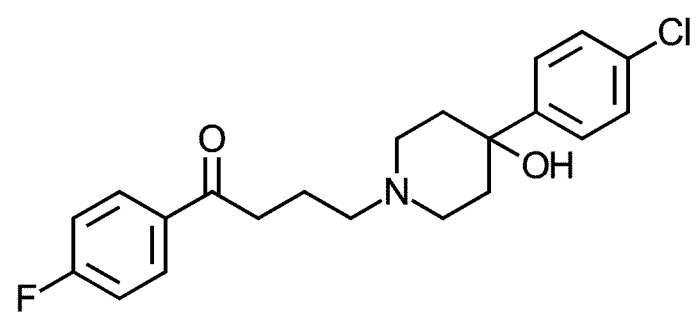
FIG. 2 shows the chemical structure of haloperidol.

The present disclosure provides a salt of Formula IIb:

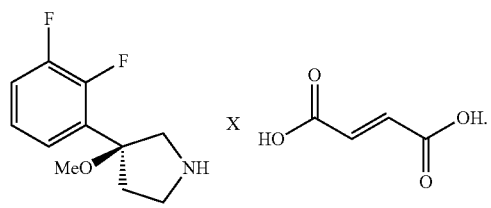

Formula IIb

The present disclosure also provides a process for manufacturing a salt of Formula IIb: said process comprising:
resolution of a compound of Formula I:

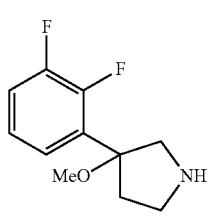

Formula I by combining said compound of Formula I with (−)-dibenzoyl-L-tartaric acid in the presence of at least one solvent thereby providing a salt of Formula IIa:

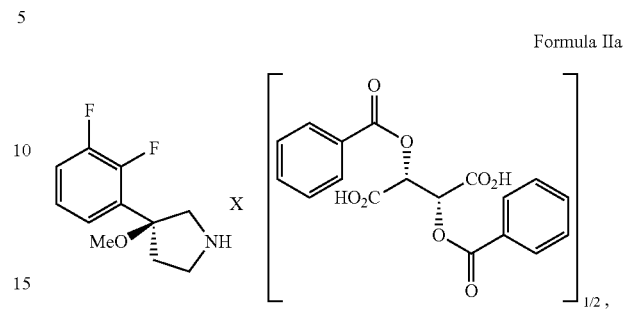

Formula IIa optionally isolating and drying the salt of Formula IIa,
removing the (−)-dibenzoyl-L-tartaric acid from the salt of Formula IIa thereby providing a compound of Formula II,

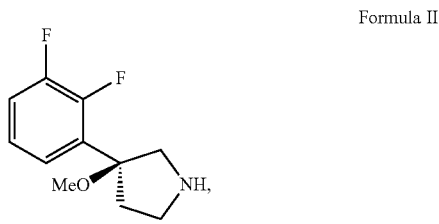 [SMILES: CO[C@]1(c2cccc(F)c2F)CCNC1]

Formula II and
combining the compound of Formula II with fumaric acid thereby providing the salt Formula IIb.

Further, the present disclosure also provides a salt of Formula IIa:

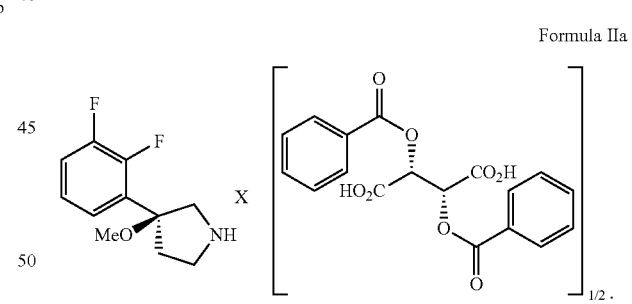

Formula IIa

The present disclosure also provides a process for manufacturing a compound of Formula II:

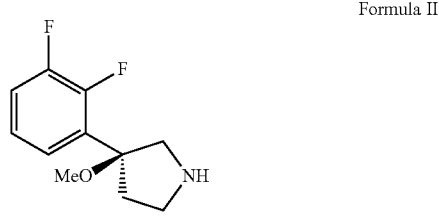 [SMILES: CO[C@]1(c2cccc(F)c2F)CCNC1]

Formula II or a pharmaceutically acceptable salt thereof,
said process comprising:
resolution of a compound of Formula I:

Formula I

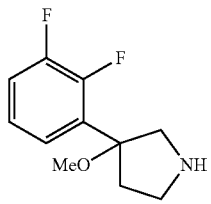

by combining said compound of Formula I with (−)-dibenzoyl-L-tartaric acid in the presence of at least one solvent thereby providing a salt of Formula IIa:

Formula IIa

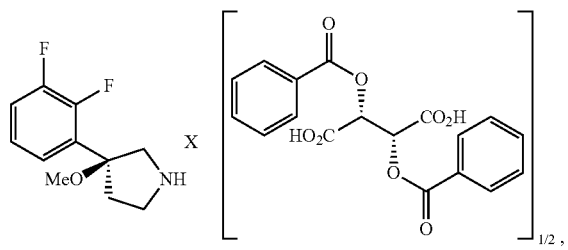

optionally isolating and drying the salt of Formula IIa,
removing the (−)-dibenzoyl-L-tartaric acid from the salt of Formula IIa thereby providing the compound of Formula II, and
optionally combining the compound of Formula II with a pharmaceutically acceptable acid thereby providing a pharmaceutically acceptable salt of the compound of Formula II.

The present disclosure also provides a method for manufacturing a compound of Formula I as described herein:
said method comprising the steps of:
reacting a compound of Formula IV, such as a Grignard reagent prepared from bromo-2,3-difluorobenzene, with a compound of Formula V to provide a compound of Formula VI:

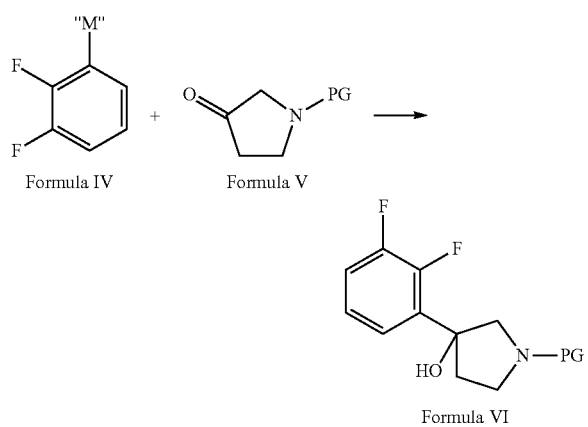

wherein:
"M" represents an alkali metal or an alkaline earth metal halide,
PG represents a protecting group such as tert-butoxycarbonyl,
subjecting the compound of Formula VI to recrystallization from at least one solvent consisting of or comprising cyclohexane,
converting the compound of Formula VI into the compound of Formula VII:

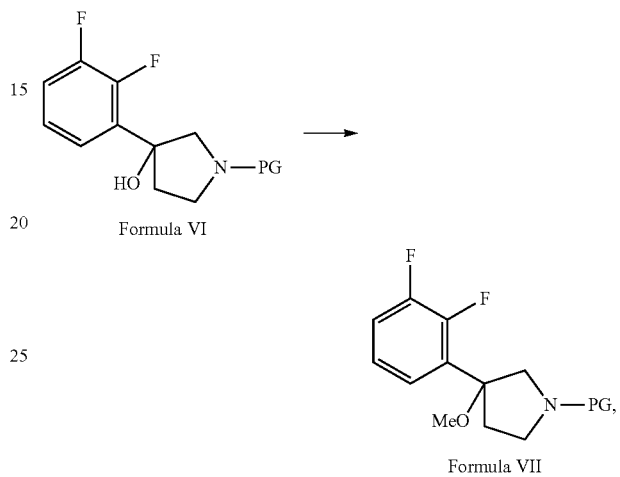

and
removing the protecting group from the compound of Formula VII thereby providing the compound of Formula I:

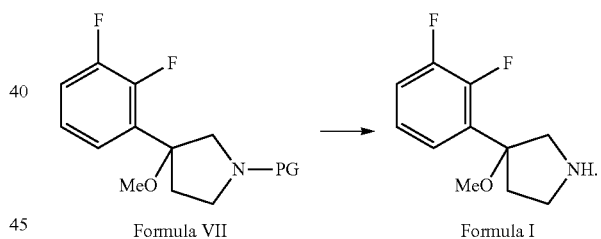

The present disclosure also provides a pharmaceutical composition comprising:
a salt of Formula IIa, Formula IIa', Formula IIb or Formula IIb' as described herein; or
a compound of Formula II, or a pharmaceutically acceptable salt thereof, obtainable by the process described herein,
in admixture with a pharmaceutically acceptable excipient, carrier and/or diluent.

The present disclosure also provides
a salt of Formula IIa, Formula IIa', Formula IIb or Formula IIb' as described herein; or
a compound of Formula II, or a pharmaceutically acceptable salt thereof, obtainable by the process described herein,
for use as a medicament in therapy.

The present disclosure also provides
a salt of Formula IIa, Formula IIa', Formula IIb or Formula IIb' as described herein; or
a compound of Formula II, or a pharmaceutically acceptable salt thereof, obtainable by the process described herein,
for use in the treatment and/or prevention of a disease, disorder and/or condition which is at least one of the following: dementia, age-related cognitive impairment, Autism spectrum disorder, ADHD, Cerebral Palsy, Huntington's disease, Gilles de la Tourette's syndrome, depression, bipolar disorder, schizophrenia, schizophreniform disorder, generalized anxiety disorder (GAD), specific phobia, panic disorder, sleep disorder, bipolar disorder, drug induced psychotic disorder, iatrogenic psychosis, iatrogenic hallucinosis, non-iatrogenic psychosis, non-iatrogenic hallucinose, mood disorder, anxiety disorder, depression, obsessive-compulsive disease, emotional disturbances related to ageing, Alzheimer's disease, Parkinson's disease dementia, behavioural and psychological symptoms of dementia, substance abuse, disorders characterized by misuse of food, sexual disorders, eating disorder, obesity, headache, pains in conditions characterized by increased muscular tone, movement disorder, Parkinson's disease, Parkinsonism, parkinsonian syndromes, dyskinesia, L-DOPA induced dyskinesia, dystonia, neurodevelopmental disorder, neurodegenerative disorder, tics, tremor, restless legs, narcolepsy, behavioural disorder.

The present disclosure also provides use of a salt of Formula IIa, Formula IIa', Formula IIb or Formula IIb' as described herein; or a compound of Formula II, or a pharmaceutically acceptable salt thereof, obtainable by the process described herein, for the manufacture of a medicament for use in the treatment and/or prevention of a disease, disorder and/or condition which is at least one of the following: dementia, age-related cognitive impairment, Autism spectrum disorder, ADHD, Cerebral Palsy, Huntington's disease, Gilles de la Tourette's syndrome, depression, bipolar disorder, schizophrenia, schizophreniform disorder, generalized anxiety disorder (GAD), specific phobia, panic disorder, sleep disorder, bipolar disorder, drug induced psychotic disorder, iatrogenic psychosis, latrogenic hallucinosis, non-iatrogenic psychosis, non-iatrogenic hallucinose, mood disorder, anxiety disorder, depression, obsessive-compulsive disease, emotional disturbances related to ageing, Alzheimer's disease, Parkinson's disease dementia, behavioural and psychological symptoms of dementia, brain injury, substance abuse, disorders characterized by misuse of food, sexual disorders, eating disorder, obesity, headache, pains in conditions characterized by increased muscular tone, movement disorder, Parkinson's disease, Parkinsonism, parkinsonian syndromes, dyskinesia, L-DOPA induced dyskinesia, dystonia, neurodevelopmental disorder, neurodegenerative disorder, tics, tremor, restless legs, narcolepsy, behavioural disorder.

The present disclosure also provides a method for treatment and/or prevention of a disease, disorder and/or condition which is at least one of the following: dementia, age-related cognitive impairment, Autism spectrum disorder, ADHD, Cerebral Palsy, Huntington's disease, Gilles de la Tourette's syndrome, depression, bipolar disorder, schizophrenia, schizophreniform disorder, generalized anxiety disorder (GAD), specific phobia, panic disorder, sleep disorder, bipolar disorder, drug induced psychotic disorder, iatrogenic psychosis, latrogenic hallucinosis, non-iatrogenic psychosis, non-iatrogenic hallucinose, mood disorder, anxiety disorder, depression, obsessive-compulsive disease, emotional disturbances related to ageing, Alzheimer's disease, Parkinson's disease dementia, behavioural and psychological symptoms of dementia, brain injury, substance abuse, disorders characterized by misuse of food, sexual disorders, eating disorder, obesity, headache, pains in conditions characterized by increased muscular tone, movement disorder, Parkinson's disease, Parkinsonism, parkinsonian syndromes, dyskinesia, L-DOPA induced dyskinesia, dystonia, neurodevelopmental disorder, neurodegenerative disorder, tics, tremor, restless legs, narcolepsy, behavioural disorder; comprising administering to a mammal, such as a human or an animal, in need thereof an effective amount of a salt of Formula IIa, Formula IIa', Formula IIb or Formula IIb' as described herein; or a compound of Formula II, or a pharmaceutically acceptable salt thereof, obtainable by the process described herein.

DESCRIPTION

The present disclosure provides a salt of Formula IIb:

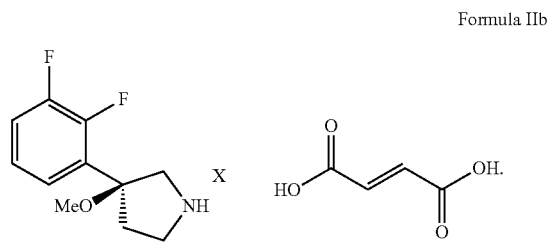

Formula IIb

Thus, the salt of Formula IIb is a combination of a compound of Formula II and fumaric acid in a 1:1 ratio. In other words, the salt of Formula IIb is a fumaric acid salt of the compound of Formula II wherein the ratio of the fumaric acid and the compound of Formula II is 1:1.

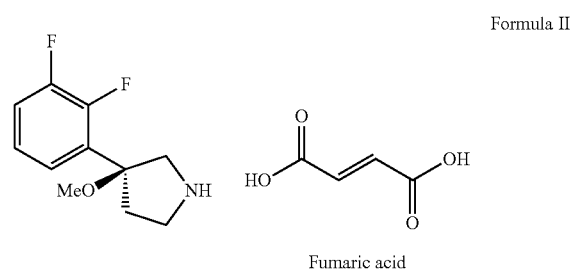 [SMILES: CO[C@]1(c2cccc(F)c2F)CCNC1 ; O=C(O)/C=C/C(=O)O]

Formula II

Fumaric acid

The salt of Formula IIb is pharmaceutically acceptable and has unexpectedly been found to exhibit properties of high crystallinity (i.e. being substantially crystalline), not being hygroscopic, not changing in its crystalline phase at any tested relative humidity, high melting point and/or acceptable aqueous solubility profile. Furthermore, the salt of Formula IIb can be isolated in good chemical yield with a high purity.

Thus, there is provided a salt of Formula IIb as described herein, characterized by being crystalline. The crystallinity may be determined by XRPD or any other appropriate method. The high crystallinity of the salt of Formula IIb which makes it well-defined with respect to, for instance, melting point and XRPD, is a benefit in making tablets and is believed to enhance storage stability. In this document, high crystallinity intends a degree of crystallinity of about 80% or more such as about 85%, about 90%, about 95%, about 99% or about 100% as measured by XPRD or any other appropriate method of measurement.

The fact that the salt of Formula IIb is not hygroscopic is advantageous since it allows for storage without being changed by surrounding humidity. It has been found that the salt of Formula IIb changes its weight by ±0.2% by weight or less at any humidity such as any relative humidity as described herein, i.e. it is not hygroscopic or substantially not hygroscopic. In an example, the salt of Formula IIb does not change its weight at any humidity such as any tested relative humidity.

Further, it is advantageous that the salt of Formula IIb does not change its crystalline phase at any humidity such as any relative humidity as described herein making it storage stable.

The high melting point of the salt of Formula IIb of about 164.1° C. is a benefit in, for instance, tablet making. Further, the water solubility of the salt of Formula IIb has been found to be 34 mg/mL and/or 74.1 mg/mL at room temperature as measured in a regular water solubility test and flask method water solubility test, respectively, as described in the Examples section of this document making it suitable for any administration to a human, such as oral administration.

It will be appreciated that the humidity such as any relative humidity may be within the range of from about 0 to about 100%. For instance, the humidity such as the relative humidity may be within the range of from about 0 to about 97%. In an example, the humidity such as the relative humidity may be equal to or above at least one of the following: about 0%, about 6%, about 11%, about 22%, about 32%, about 43%, about 56%, about 73%, about 84%, about 97%. The humidity such as the relative humidity may be measured at a temperature within the range of from about 20° C. to about 50° C. For instance, the humidity such as the relative humidity may be about 30° C. The weight of the salt of Formula IIb may be determined after storage for about one week at a humidity such as a relative humidity as described herein and/or at a temperature as described herein.

There is also provided a salt of Formula IIb as described herein having a melting point of from about 163° C. to about 165° C. such as about 164.1° C. The melting point may be determined by differential scanning calorimethry (DSC). Further, the salt of Formula IIb described herein may have a a water solubility from about 30 mg/mL to about 80 mg/mL as determined by the regular water solubility test method and/or the flask method water solubility test described in the Examples section of this document. For instance, the water solubility of the salt of Formula IIb may be 34 mg/mL as determined by the regular water solubility method described herein and/or 74.1 mg/mL as determined by the flask method water solubility test described herein. The water solubility may be measured at room temperature, i.e. a temperature within the range of from about 22° C. to about 25° C.

In this document, the relative humidity intends the ratio of the partial pressure of water vapour to the equilibrium pressure of water at a given temperature and at atmospheric pressure.

The salt of Formula IIb may be characterized by an XRPD diffractogram comprising a peak at about 23.16 2θ, and optionally at least one further peak selected from the following: about 6.66 such as about 6.7, about 13.41 such as about 13.4, about 27.79 such as about 27.8, about 29.38 such as about 29.4 2θ. The salt of Formula IIb may also be characterized by an XRPD diffractogram comprising a peak at about 6.66, about 13.41, about 23.16, about 27.79, about 29.38 2θ, and optionally at least one further peak selected from the following: about 16.27, about 34.02 2θ. For instance, the XRPD diffractogram may comprise peaks at about 6.7, about 13.4, about 23.2, about 27.8 and about 29.4 2θ. The salt of Formula IIb may also be characterized by an XRPD diffractogram comprising a peak at about 6.66, about 13.41, about 16.27, about 23.16, about 27.79, about 29.38, about 34.02 2θ, and optionally at least one further peak selected from the following: about 16.42, about 21.69 2θ.

The salt of Formula IIb may be characterized by an XRPD diffractogram substantially as shown in FIG. 1.

Additionally or alternatively, the compound of Formula II may be combined with fumaric acid in a 2:1 ratio thereby forming a salt of Formula IIb':

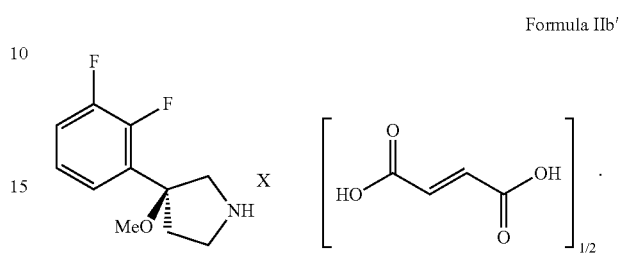

Formula IIb'

The salt of Formula IIb' may be manufactured using a process as described herein.

The present disclosure provides a process for manufacturing the salt of Formula IIb:

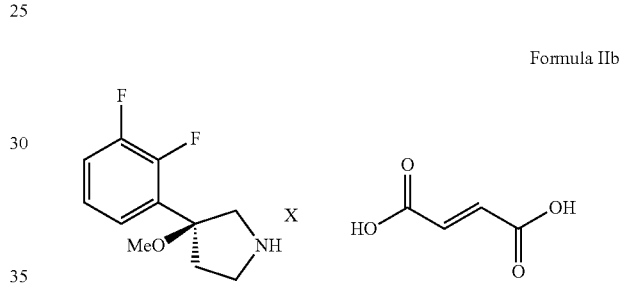

Formula IIb said process comprising:
resolution of a compound of Formula I:

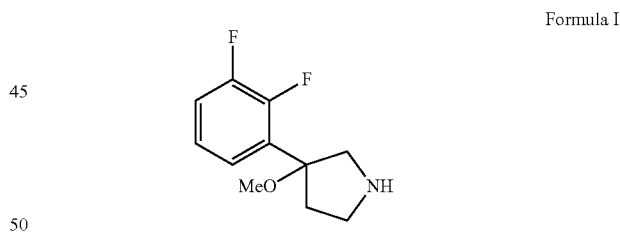

Formula I by combining said compound of Formula I with (−)-dibenzoyl-L-tartaric acid in the presence of at least one solvent thereby providing a salt of Formula IIa:

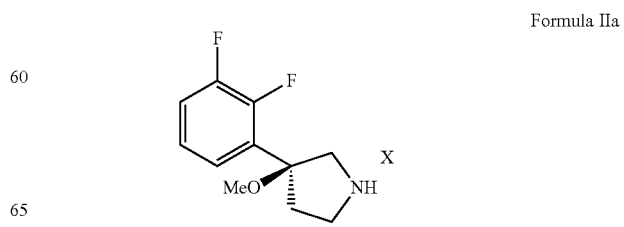

Formula IIa

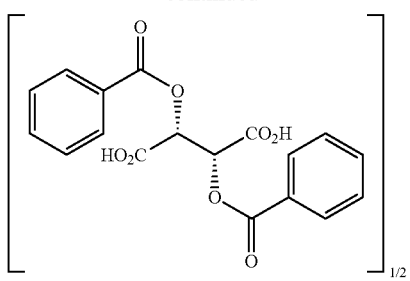

optionally drying and/or isolating the salt of Formula IIa, removing the (−)-dibenzoyl-L-tartaric acid from the salt of Formula IIa thereby providing the compound of Formula II e.g. by treating the salt of Formula IIa with a base:

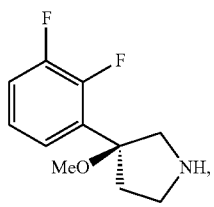

Formula II and combining the compound of Formula II with fumaric acid to provide the salt of Formula IIb.

It will be appreciated that the salt of Formula IIb may also be prepared by combining fumaric acid with a compound of Formula II, which compound of Formula II has been prepared using a chiral resolution process different from the one described herein. For instance, the compound of Formula II may be prepared by fractional crystallization of a diastereomeric salt of a compound of Formula I which is different from the salt with (−)-dibenzoyl-L-tartaric acid such as for instance a salt with other tartrate derivatives such as (−)-di-p-toluyl-L-tartaric acid. Other resolution procedures for preparing the compound of Formula II may be a resolution procedure utilizing a derivative of the compound of Formula I rather than the compound of Formula I itself such as for instance utilizing an N-benzyl derivative of a compound of Formula I. Such a procedure may comprise a fractional crystallization step utilizing a diastereomeric salt such as for instance a salt with (−)-dibenzoyl-L-tartaric acid, and/or the procedure may comprise a chromatographic separation step as depicted in Scheme 1. Further, a resolution procedure comprising a chromatographic separation step may be a process where the two enantiomers of a compound of Formula I are directly separated on a chiral column for chromatography. Further, the compound of Formula II may be prepared using asymmetric synthesis or by any other method known in the art.

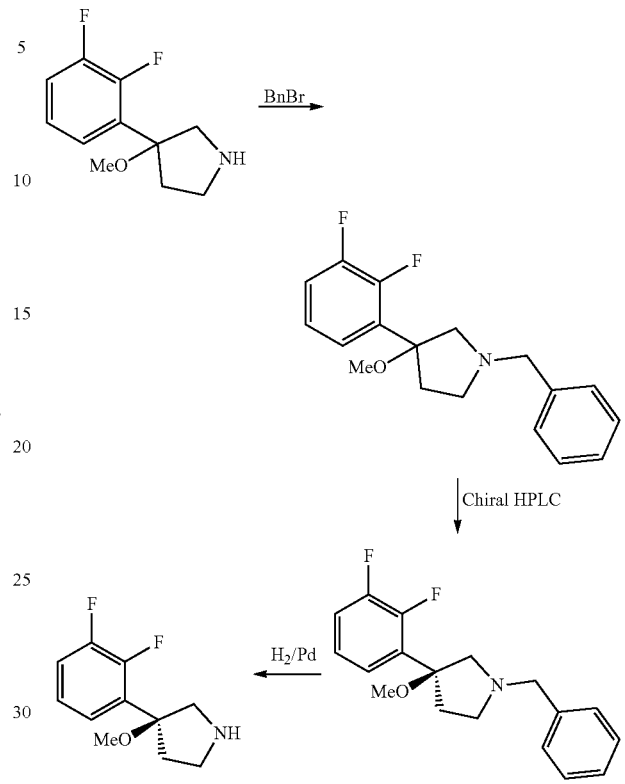

Scheme 1

The present disclosure also provides a process for manufacturing a compound of Formula II:

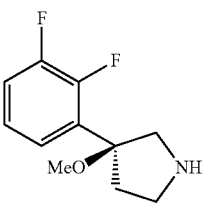

Formula II or a pharmaceutically acceptable salt thereof, said process comprising:

resolution of a compound of Formula I:

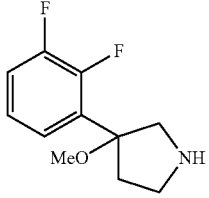

Formula I by combining said compound of Formula I with (−)-dibenzoyl-L-tartaric acid in the presence of at least one solvent thereby providing a salt of Formula IIa:

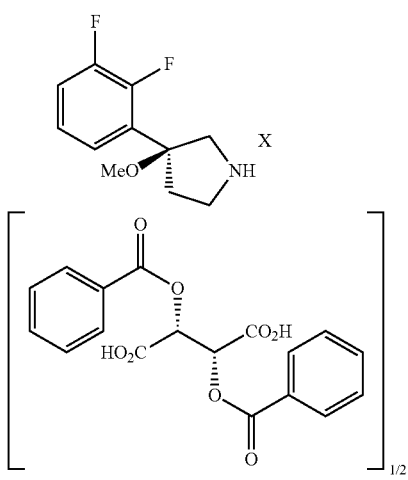

Formula IIa

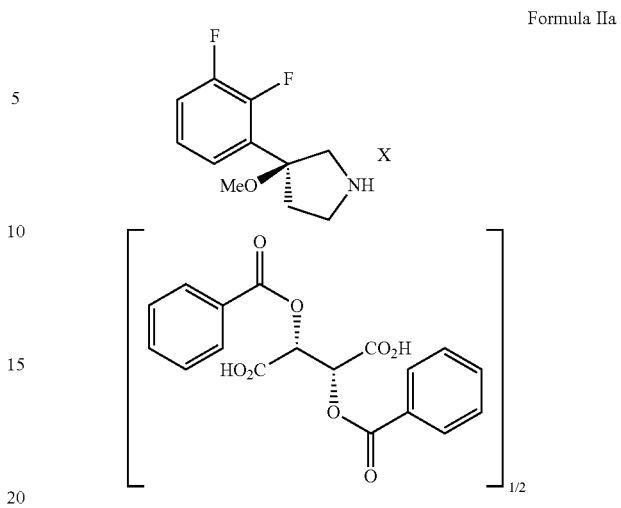

Formula IIa optionally drying and/or isolating the salt of Formula IIa,
removing the (−)-dibenzoyl-L-tartaric acid from the salt of Formula IIa thereby providing the compound of Formula II,
and
optionally combining the compound of Formula II with a pharmaceutically acceptable acid thereby providing a pharmaceutically acceptable salt of the compound of Formula II.

The (−)-dibenzoyl-L-tartaric acid may be removed from the salt of Formula IIa by treating the salt of Formula IIa with a base or an ion exchanger.

Thus, there is a process for manufacturing a compound of Formula II:

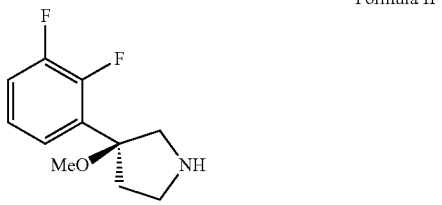

Formula II or a pharmaceutically acceptable salt thereof,
said process comprising:
resolution of a compound of Formula I:

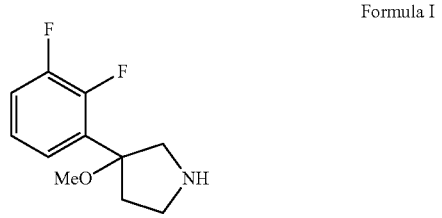 [SMILES: COC1(c2cccc(F)c2F)CCNC1]

Formula I by combining said compound of Formula I with (−)-dibenzoyl-L-tartaric acid in the presence of at least one solvent thereby providing a salt of Formula IIa:

optionally drying and/or isolating the salt of Formula IIa,
treating the compound of Formula IIa with a base, or treating the compound of Formula IIa with an ion exchange resin followed by treatment with a base, thereby providing the compound of Formula II, and
optionally combining the compound of Formula II with a pharmaceutically acceptable acid thereby providing a pharmaceutically acceptable salt of the compound of Formula II.

It will be appreciated that the compound of Formula I described herein is an enantiomeric mixture. The enantiomeric mixture may be a racemate, i.e. a 50:50 mixture of enantiomers. In this document, the compound of Formula I is also denominated 3-(2,3-difluorophenyl)-3-methoxypyrrolidine.

Further, it will be appreciated that the compound of Formula II described herein is the (+)-enantiomer of the compound of Formula I and is substantially enantiomerically pure, i.e. it is substantially free of the (−)-enantiomer of the compound of Formula I and may have an enantiomeric excess of about 95% or more such as 96%, 97%, 98% or 99%. In this document, the compound of Formula II is also denominated (+)-3-(2,3-difluorophenyl)-3-methoxypyrrolidine. Further, determination of the absolute configuration as described herein showed S-configuration for the compound of Formula II. Thus, the compound of Formula II may also be denominated. (S)-3-(2,3-difluorophenyl)-3-methoxypyrrolidine.

The pharmaceutically acceptable salts of the compound of Formula II may be acid addition salts selected from the group consisting of: hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate, toluene-p-sulphonate, and any combination thereof. As an example, the pharmaceutically acceptable salt may be a fumarate salt formed from fumaric acid and the compound of Formula II.

The processes described herein for manufacturing the salt of Formula IIb, or the compound of Formula II, or a pharmaceutically acceptable salt thereof, comprise chiral resolution, wherein said chiral resolution may include the steps of:

a) dissolving the (−)-dibenzoyl-L-tartaric acid in the at least one solvent, optionally by heating, to provide a first solution, b) adding a solution comprising the compound of Formula I and at least one further solvent to said first solution thereby providing a second solution, and c) precipitating the salt of Formula IIa, optionally by cooling, from said second solution.

For instance, step a) may be performed during heating in order to dissolve the (−)-dibenzoyl-L-tartaric acid in the at least one solvent. Step b) may then be performed while the first solution is warm. Upon cooling the second solution the salt of Formula IIa will precipitate from said second solution. Additionally or alternatively, the salt of Formula IIa may precipitate from said second solution using other known crystallization techniques known in the art such as addition of a seed crystal. The salt of Formula IIa may subsequently be washed with the at least one further solvent and/or dried.

The at least one solvent and/or the at least one further solvent as described herein may be selected from the group consisting of: methanol, ethanol, 1-propanol, 2-propanol, 1-butanol, 2-butanol, and any combination thereof. For instance, the at least one solvent and/or the at least one further solvent may consist of or comprise ethanol.

The treatment with the base of the process described herein may comprise the steps of:

mixing the compound of Formula IIa with a mixture of a first water-insoluble solvent and an aqueous solution comprising a base, thereby forming:

(i) a solvent phase comprising the first water-insoluble solvent, and (ii) an aqueous phase comprising the aqueous solution comprising the base, extracting (ii) with a second water-insoluble solvent to provide:

(iii) at least one phase comprising the second water-insoluble solvent, combining the phases (i) and (iii), evaporating the first and second water-insoluble solvents from the combined phases (i) and (iii) thereby providing the compound of Formula II, optionally converting the compound of Formula II into a pharmaceutically acceptable salt thereof.

In this document, a water-insoluble solvent intends an organic solvent or mixture of organic solvents that is/are substantially immiscible with water. Examples of water-insoluble solvents include dichloromethane and methyl tert-butyl ether.

For instance, the base described herein may consist of or comprise a carbonate such as sodium carbonate and/or potassium carbonate, and/or the first water-insoluble solvent and/or the second water-insoluble solvent consist(s) of or comprise(s) dichloromethane.

In the process described herein, the molar ratio between the compound of Formula I and the (−)-dibenzoyl-L-tartaric acid may be within the range of from about 1.9:1 to about 2.1: such as 2:1.

In the process described herein, the salt of Formula IIb' may be precipitated from an ethanol solution comprising the compound of Formula II and (−)-dibenzoyl-L-tartaric acid.

Advantageously, the process described herein may provide the salt of Formula IIb, and/or the compound of Formula II, or a pharmaceutically acceptable salt thereof, in high enantiomeric purity. For instance, the enantiomeric excess may be 95% or higher such as 96, 97, 98 or 99%. In this document, enantiomeric excess (ee) intends the percentage of the (+)-enantiomer of Formula I or a salt thereof minus the percentage of the (−)-enantiomer of Formula I or a salt thereof. For example, if a mixture contains 98 mole % of a (+)-enantiomer and 2 mole % of a (−)-enantiomer the enantiomeric excess is 96%.

Moreover, the present disclosure provides for manufacturing the salt of Formula IIb and/or the compound of Formula II, or a pharmaceutically acceptable salt thereof, such as a salt in high chemical purity, such as 95% or more as measured by HPLC or any other appropriate method, by incorporating into the process described herein the following method steps for preparing the compound of Formula I:

reacting a compound of Formula IV, such as a Grignard reagent prepared from bromo-2,3-difluorobenzene, with a compound of Formula V to provide a compound of Formula VI:

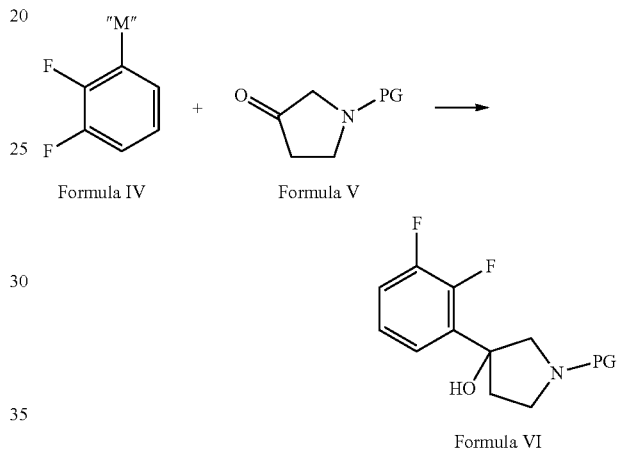

wherein:

"M" represents an alkali metal or an alkaline earth metal halide,

PG represents a protecting group such as tert-butoxycarbonyl, subjecting the compound of Formula VI to recrystallization from at least one solvent consisting of or comprising cyclohexane, converting the compound of Formula VI into the compound of Formula VII:

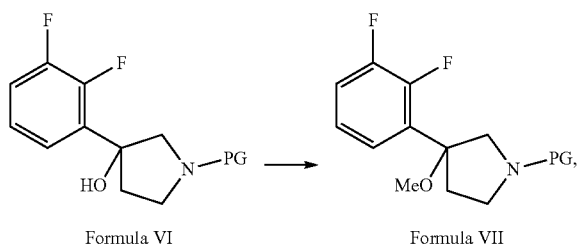

and removing the protecting group from the compound of Formula VII thereby providing the compound of Formula I:

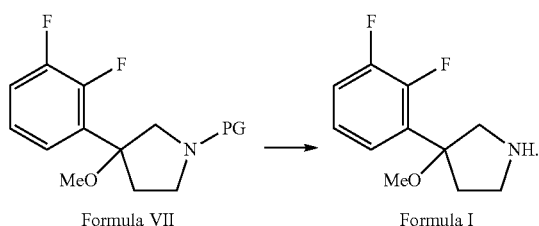

Formula VII → Formula I

Advantageously, it has been found that the method steps above substantially prevent the formation of impurities such as a compound of Formula VIII thereby avoiding or minimizing the need for additional purification steps. Previously, it was found that the compound of Formula VIII formed when tert-butyl 3-oxopyrrolidine-1-carboxylate was subjected to harsh basic conditions such as n-hexyllithium and was difficult to remove. The method described herein allows for providing the compound of Formula I in a chemical purity of about 98% or more as measured by, for instance, HPLC or NMR.

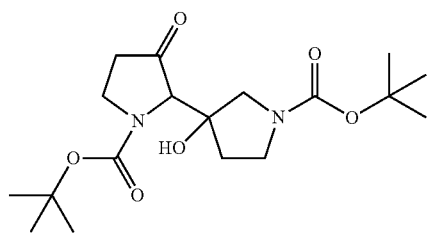

Formula VIII

There is also provided a salt of Formula IIb obtainable by a process as described herein.

There is also provided a compound of Formula II, or a pharmaceutically acceptable salt thereof, obtainable by a process as described herein.

Further, there is provided a salt of Formula IIa:

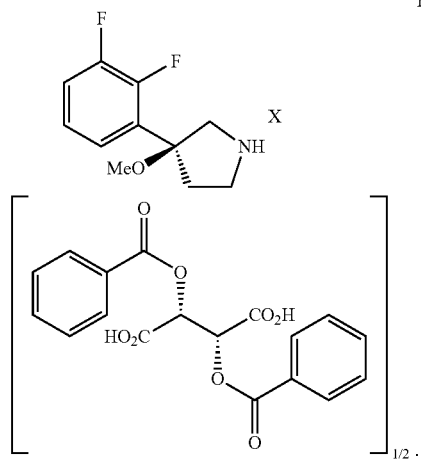

Formula IIa

The salt of Formula IIa comprises a combination of the compound of Formula II as described herein with (−)-dibenzoyl-L-tartaric acid in a ratio of 2:1. Additionally or alternatively, the compound of Formula II as described herein may be combined with (−)-dibenzoyl-L-tartaric acid in a ratio of 1:1 thereby providing a compound of Formula IIa':

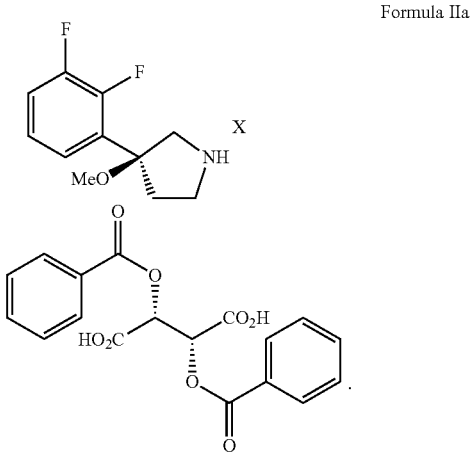

Formula IIa'

The salt of Formula IIa' may be manufactured using a process as described herein.

The salt of Formula IIa may be used as an intermediate in the manufacturing of the compound of Formula II. Additionally or alternatively, the salt of Formula IIa may also be used as an intermediate in the manufacturing of a pharmaceutically acceptable salt of the compound of Formula II such as in the manufacturing of a salt of Formula IIb. For instance, the salt of Formula IIa may also be used as an intermediate in the manufacturing of the salt of Formula IIb. The salt of Formula IIa has superior properties for the resolution process described herein which provides a high chemical yield of the salt of Formula IIa with an unexpectedly high stereochemical purity already after one crystallization. Further, crystals of the salt of Formula IIa' can be used for determining the absolute configuration of the two enantiomers of the compound of Formula II. Additionally or alternatively, the salt of Formula IIa or Formula IIa' may be used as a medicament such as a medicament for the treatment of the diseases and/or disorders described herein.

There is also provided a pharmaceutical composition comprising:

a salt of Formula IIa, Formula IIa', Formula IIb and/or Formula IIb'; and/or a compound of Formula II, or a pharmaceutically acceptable salt thereof, obtainable by the process described herein, in admixture with a pharmaceutically acceptable excipient, carrier and/or diluent.

Further, there is provided:

a salt of Formula IIa, Formula IIa', Formula IIb and/or Formula IIb'; and/or a compound of Formula II, or a pharmaceutically acceptable salt thereof, obtainable by the process described herein, for use as a medicament in therapy.

Further, there is provided:

a salt of Formula IIa, Formula IIa', Formula IIb and/or Formula IIb'; and/or a compound of Formula II, or a pharmaceutically acceptable salt thereof, obtainable by the process described herein, for use in the treatment and/or prevention of a disease, disorder and/or condition which is at least one of the following: dementia, age-related cognitive impairment, Autism spectrum disorder, ADHD, Cerebral Palsy, Huntington's disease, Gilles de la Tourette's syndrome, depression, bipolar disorder, schizophrenia, schizophreniform disorder, generalized anxiety disorder (GAD), specific phobia, panic disorder, sleep disorder, bipolar disorder, drug induced psychotic disorder, iatrogenic psychosis, iatrogenic hallucinosis, non-iatrogenic psychosis, non-iatrogenic hallucinose, mood disorder, anxiety disorder, depression, obsessive-compulsive disease, emotional disturbances related to ageing, Alzheimer's disease, Parkinson's disease dementia, behavioural and psychological symptoms of dementia, substance abuse, disorders characterized by misuse of food, sexual disorders, eating disorder, obesity, headache, pains in conditions characterized by increased muscular tone, movement disorder, Parkinson's disease, Parkinsonism, parkinsonian syndromes, dyskinesia, L-DOPA induced dyskinesia, dystonia, neurodevelopmental disorder, neurodegenerative disorder, tics, tremor, restless legs, narcolepsy, behavioural disorder.

Further, there is provided:

a salt of Formula IIa, Formula IIa', Formula IIb and/or Formula IIb'; and/or a compound of Formula II, or a pharmaceutically acceptable salt thereof, obtainable by the process described herein, for use in the treatment and/or prevention of a disease, disorder and/or condition which is Parkinson's disease dementia, behavioural and/or psychological symptoms of dementia.

There is also provided:

use of a salt of Formula IIa, Formula IIa', Formula IIb and/or Formula IIb'; and/or a compound of Formula II, or a pharmaceutically acceptable salt thereof, obtainable by the process described herein, for the manufacture of a medicament for use in the treatment and/or prevention of a disease, disorder and/or condition which is at least one of the following: dementia, age-related cognitive impairment, Autism spectrum disorder, ADHD, Cerebral Palsy, Huntington's disease, Gilles de la Tourette's syndrome, depression, bipolar disorder, schizophrenia, schizophreniform disorder, generalized anxiety disorder (GAD), specific phobia, panic disorder, sleep disorder, bipolar disorder, drug induced psychotic disorder, iatrogenic psychosis, Iatrogenic hallucinosis, non-iatrogenic psychosis, non-iatrogenic hallucinose, mood disorder, anxiety disorder, depression, obsessive-compulsive disease, emotional disturbances related to ageing, Alzheimer's disease, Parkinson's disease dementia, behavioural and psychological symptoms of dementia, brain injury, substance abuse, disorders characterized by misuse of food, sexual disorders, eating disorder, obesity, headache, pains in conditions characterized by increased muscular tone, movement disorder, Parkinson's disease, Parkinsonism, parkinsonian syndromes, dyskinesia, L-DOPA induced dyskinesia, dystonia, neurodevelopmental disorder, neurodegenerative disorder, tics, tremor, restless legs, narcolepsy, behavioural disorder.

There is also provided:

use a salt of Formula IIa, Formula IIa', Formula IIb and/or Formula IIb'; and/or a compound of Formula II, or a pharmaceutically acceptable salt thereof, obtainable by the process described herein, for the manufacture of a medicament for use in the treatment and/or prevention of a disease, disorder and/or condition which is Parkinson's disease dementia, behavioural and/or psychological symptoms of dementia.

There is also provided a method for treatment and/or prevention of a disease, disorder and/or condition which is at least one of the following: dementia, age-related cognitive impairment, Autism spectrum disorder, ADHD, Cerebral Palsy, Huntington's disease, Gilles de la Tourette's syndrome, depression, bipolar disorder, schizophrenia, schizophreniform disorder, generalized anxiety disorder (GAD), specific phobia, panic disorder, sleep disorder, bipolar disorder, drug induced psychotic disorder, iatrogenic psychosis, Iatrogenic hallucinosis, non-iatrogenic psychosis, non-iatrogenic hallucinose, mood disorder, anxiety disorder, depression, obsessive-compulsive disease, emotional disturbances related to ageing, Alzheimer's disease, Parkinson's disease dementia, behavioural and psychological symptoms of dementia, brain injury, substance abuse, disorders characterized by misuse of food, sexual disorders, eating disorder, obesity, headache, pains in conditions characterized by increased muscular tone, movement disorder, Parkinson's disease, Parkinsonism, parkinsonian syndromes, dyskinesia, L-DOPA induced dyskinesia, dystonia, neurodevelopmental disorder, neurodegenerative disorder, tics, tremor, restless legs, narcolepsy, behavioural disorder;

comprising administering to a mammal, such as a human or an animal, in need thereof an effective amount of a salt of Formula IIa, Formula IIa', Formula IIb and/or Formula IIb'; and/or a compound of Formula II, or a pharmaceutically acceptable salt thereof, obtainable by the process described herein.

There is also provided a method for treatment and/or prevention of a disease, disorder and/or condition which is Parkinson's disease dementia, behavioural and/or psychological symptoms of dementia, comprising administering to a mammal, such as a human or an animal, in need thereof an effective amount of a salt of Formula IIa, Formula IIa', Formula IIb and/or Formula IIb'; and/or a compound of Formula II, or a pharmaceutically acceptable salt thereof, obtainable by the process described herein.

The diseases, disorders and/or conditions described herein are associated at least partly with the sigma-1-receptor (i.e. σ-1-receptor), said receptor being expressed in many tissue types and being particularly concentrated in certain regions of the central nervous system. Therefore, it is believed that a compound or salt thereof as described herein that exhibits interaction with the sigma-1-receptor is useful in the treatment and/or prevention of a disease, disorder and/or condition as described herein. For example, the compounds and salts thereof as described herein are considered useful in the treatment and/or prevention of the diseases, disorders and/or conditions described herein when they interact with the sigma-1-receptor in a radioligand binding assay as described in this document to displace at least about 50%, at least about 60% or at least about 70% of haloperidol.

The present disclosure also provides a method for preparing a compound of Formula I, said method comprising the steps of:

reacting a compound of Formula IV, such as a Grignard reagent prepared from bromo-2,3-difluorobenzene, with a compound of Formula V to provide a compound of Formula VI:

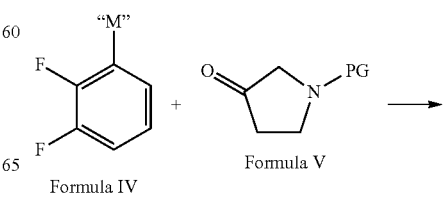

Formula IV  Formula V

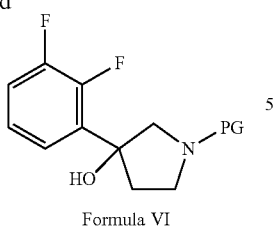

Formula VI wherein:
"M" represents an alkali metal or an alkaline earth metal halide,
PG represents a protecting group such as tert-butoxycarbonyl,
subjecting the compound of Formula VI to recrystallization from at least one solvent consisting of or comprising cyclohexane,
converting the compound of Formula VI into the compound of Formula VII:

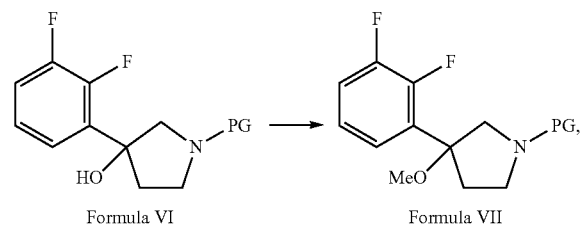

Formula VI → Formula VII and
removing the protecting group from the compound of Formula VII thereby providing the compound of Formula I:

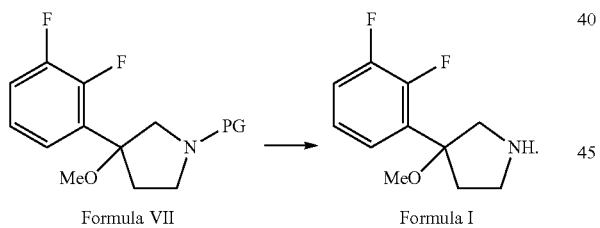

Formula VII → Formula I

It will be appreciated that when the compound of Formula IV is a Grignard reagent it may be prepared as known in the art. In particular, it may be prepared using a Grignard reagent as described in EP 1 582 524 A1, which is incorporated herein by reference. Thus, "M" of the compound of Formula IV may be $(MgX)_n$ LiY wherein X and Y may be Cl, Br or I.

Advantageously, it has been found that the method steps above substantially prevent the formation of impurities such as formation of a compound of Formula VIII described herein thereby avoiding or minimizing the need for additional purification steps. The method may provide the compound of Formula I in a chemical purity of about 98% or more as measured by, for instance, HPLC or NMR.

The conversion of the compound of Formula VI into the compound of Formula VII may be performed using standard procedures such as using methyl iodide in the presence of a base such as potassium tert-butoxide. The removal of the protecting group may be performed using standard procedures such as using acid conditions such as in the presence of strong acidic conditions.

Salts

In this document, the chemical structure of the salts comprising a combination of the compound of Formula II and an acid have been drawn as a complex wherein the acidic proton(s) of the acid is attached to the acid. However, the skilled person understands that the acidic proton(s) of the acid may be attached to the nitrogen atom of the compound of Formula II and/or shared between the nitrogen atom of the compound of Formula II and the acid, and this is also intended to be encompassed by the complexes described herein. For instance, the salt of Formula IIb may also be represented as:

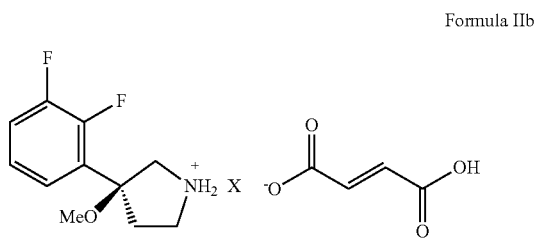

Formula IIb

In a further example, the salt of Formula IIa may be represented as:

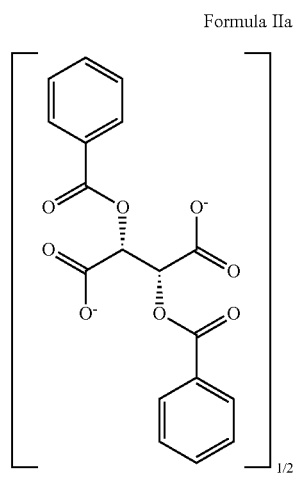

Formula IIa

It will be appreciated that the salts of Formula II described herein may be converted to another salt of Formula II using standard procedures known in the art.

Isotopes

The compounds or salts of the present disclosure may contain unnatural proportions of atomic isotopes at one or more of the atoms that constitute such compounds or salts. In case of a salt, which is a combination of a compound as described herein with an acid as described herein, the compound of said combination may contain one or more atomic isotopes, i.e. the compound may be labelled with an isotope. For example, the compounds may be labelled with one or more isotopes, such as for example tritium ($^3H$), deuterium ($^2H$), iodine-125 ($^{125}I$) or carbon-14 ($^{14}C$). In an example, the compound is labelled with one or more deuterium atoms. All isotopic variations of the compounds of the present disclosure, whether radioactive or not, are intended to be encompassed within the scope of the present disclosure.

Thus, the present disclosure provides a compound as described herein, such as a compound of Formula I, a compound of Formula II, a compound of Formula IV, a compound of Formula V, a compound of Formula VI and/or a compound of Formula VII, which is labelled with one or more isotopes such as deuterium. The compounds labelled with an isotope as described herein may be combined with an acid as described herein thereby providing a salt as described herein.

In an example, the compound of Formula II may be labelled with an isotope such as deuterium. One or more hydrogen atoms of phenyl ring, the pyrrolidine ring and/or the methoxy group of the compound of Formula II may then be replaced with an isotope such as deuterium.

The disclosure is further illustrated by the following non-limitative Examples.

EXAMPLES

In this document, unless otherwise stated, the naming and the drawing of the chemical compounds have been made using the software package J Chem for Excel, ver. 14.8.2600.753. If the name and drawing are inconsistent, the chemical structure shall be considered to be correct.

General

Reagents and solvents were used as purchased without purification.

HPLC analyses were performed on a Dionex HPLC Module with Dionex UVD 170U Detector and a Thermo Finnigan MS. Column: Waters XBridge™ C18, 4.6×50 mm, Mobile phase A: 0.1% formic acid (aq.), Mobile phase B: acetonitrile, Flow: 1 mL/min, Injection volume: 3-20 µL, Detection: 220-320 nm, Gradient: 0% to 100% B in 5 min, buffers A or C were used.

NMR analyses were performed on a Varian Mercury 400 instrument operating at 400 MHz. Residual solvent peak was used as an internal standard.

The assay and purity determination of the compounds were performed by gradient liquid chromatography with UV-detection at 260 nm except for the impurity compound of Formula VIII, which was detected at 220 nm. The compound of Formula VIII has a structure as described herein. The amount of impurities was estimated by internal normalisation. In the case when a solution of a synthetic intermediate was used in the synthesis without isolation of the intermediate, an aliquot evaporation method was employed in order to determine the chemical yield. That means that a specific volume of the solution was evaporated and the residue was analysed by chromatography and compared with that of a chromatogram of a known amount of said intermediate. Column: Hypersil Gold C18, 4.6×150 mm, 3 µm (Thermo), Column temperature: 40° C., Column oven: Dionex TCC-3000 SD, Pump: Dionex LPG-3400 SD, Flow rate: 1 mL/min, Injector: Dionex WPS-3000 SL, Injection volume: 10 µL, Detector: Dionex DAD-3000, Wavelength: 260 nm, Data collecting system: Chromeleon.

The enantiomeric purity determination of the compound of Formula II and its salts was performed by isocratic liquid chromatography with UV-detection at 220 nm. The enantiomeric purity was estimated by internal normalisation. Column: Chiralpak AD-H, 250×4.6 mm, 5 µm (Daicel), Column temperature: 25° C., Column oven: Dionex TCC-3000 SD, Pump: Dionex LPG-3400 SD, Flow rate: 0.8 mL/min, Injector: Dionex WPS-3000 SL, Injection volume: 10 µL, Detector: Dionex DAD-3000, Wavelength: 220 nm, Data collecting system: Chromeleon (Dionex).

XRPD data were collected on a Bruker D8 Advance (2005) instrument. Radiation Copper Ka, λ=1.54180 Å, Kb filter 0.020 mm Ni foil, Anode voltage: 40 kV, Anode current 40 mA, Detector: LynxEye (1D-position sensitive), Slits 0.6 mm and 8 mm, Step size 0.02°, Scan speed 0.2 s/step, Interval (2Θ) (3-35) ° in 2θ scale. X-ray crystallography was performed using a Bruker D8 Venture diffractometer equipped with a photon 100 CMOS detector. The crystal was mounted in a Kapton loop using silicone grease. Temperature: 123 K (open-flow nitrogen cooling device). Data were collected using Mo K-alpha radiation. The Apex suite of programs by Bruker were used for data-reduction.

Hygroscopicity Test

Hygroscopicity tests of the salts were performed by keeping exact weight samples of the different salts at varied humidity at 30° C. After one week, the samples were weighed again and based on the original weight the percentage weight difference was calculated.

Regular Water Solubility Test

Water solubility tests for the salts as described herein were performed as follows unless otherwise stated. 0.05 g of each salt was weighed in a flask and the mass of flask+salt (m-vs) was recorded. Water was slowly added dropwise into the flask with salt until full dissolution was achieved as observed by the naked eye. The mass of flask+salt+solvent (m-sys) was recorded. The solubility expressed as "grams of solute/kg of solvent", i.e. "grams of salt/kg of solvent", was calculated according to the equation:

$$\text{Solubility} = \frac{(s) \times 1000}{(m-svs)-(m-vs)} \qquad \text{Eq. 1}$$

In Eq. 1:

(s) stands for the weight of the salt measured in kg, (m-sys) stands for the mass of the flask+salt+solvent measured in kg, and (m-vs) stands for the mass of the flask+salt measured in kg.

The value of (s) was 0.05/1000 kg.

Since the solubility was measured in water, and water has a density of 1 g/mL the unit of the solubility may be g/L or mg/mL.

Flask Method Water Solubility Test

In some cases, a further water solubility test (Flask method water solubility test) was performed as follows. An excess of salt was added to water. The mixture was equilibrated (shaking) for at least 24 hours thereby providing a saturated salt solution. Then the saturated solution was clear-filtered and transferred into a clean pre-weighed flask (mv). The mass of flask+saturated solution (mvs) was recorded. The solvent was evaporated under reduced pressure until constant mass. Flask containing dried residue was weighed (mvdr). The solubility expressed as "grams of solute/kg of solvent", i.e. "grams of salt/kg of solvent", was calculated according to the equation:

$$\text{Solubility} = \frac{(mvdr-mv) \times 1000}{(mvs-mvdr)} \qquad \text{Eq. 2}$$

In Eq. 2:

(mvdr-mv) is the weight difference in kg between (i) the mass of the flask containing dried residue after evaporation of the solvent and (ii) the mass of the flask, and (mvs-mvdr) is the weight difference in kg between (i) the mass of the flask including the saturated salt solution and (ii) the mass of the flask containing the dried residue. Since the solubility was measured in water, and water has a density of 1 g/mL the unit of the solubility may be g/L or mg/mL.

ABBREVIATIONS

APCI Atmospheric pressure chemical ionization
Bn Benzyl
DCM dichloromethane
ee enantiomeric excess
Eq. Equation
g gram(s)
HPLC High Performance Liquid Chromatography
kg kilogram(s)
MTBE Methyl tert-butyl ether
min. minute(s)
mg milligram(s)
mL millilitre
mm millimeter
MS Mass Spectrometry
nm nanometer
M molar
mol mole
mmol(e) millimole
NMR Nuclear Magnetic Resonance
i-PrOAc Isopropyl acetate
THF Tetrahydrofurane
XRPD X Ray Powder Diffraction
UV ultraviolet
Å Angstrom Example 1

Synthesis of Crude tert-butyl 3-(2,3-difluorophenyl)-3-hydroxypyrrolidine-1-carboxylate, i.e. the Compound of Formula (VIa)

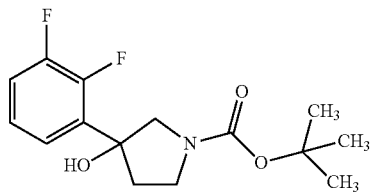

Formula VIa

MTBE (60 mL) was charged to a 3-neck round bottom flask followed by bromo-2,3-difluoro-benzene (12 mL, 107 mmol). The solution was cooled in ice/salt bath. When the internal temperature reached −4° C. addition of i-PrMgCl·LiCl solution in THF (1.3M, 90.7 mL, 118 mmol) was started. The higher internal temperature during addition was 2° C. (bath temperature was −8° C. to −5° C.); addition time 17 min. After addition was complete the reaction mixture was stirred at −5° C. to 0° C. for one hour. Tert-Butyl 3-oxopyrrolidine-1-carboxylate (21.8 g, 118 mmol) solution in MTBE (200 mL) was added to the reaction mixture at −4° C. to −2° C. during 15 min. under vigorous stirring. The reaction mixture was stirred at −2° C. to 0° C. for 3 hours and then quenched by addition of 20% aqueous ammonium chloride solution (260 mL). The internal temperature rose from 0° C. to 15° C. during addition. The cooling bath was removed and the mixture was stirred at room temperature for 1 hour. Layers were separated and the aqueous phase was re-extracted with MTBE (120 mL). Combined organic extracts were washed with brine (160 mL) and water (2×120 mL). Organic layer was concentrated to approx. 120 mL volume. MTBE (120 mL) was added and solvent evaporated to 120 mL volume left. 120 mL of MTBE was added again and evaporated till 120 mL volume left. Cyclohexane (120 mL) was added and mixture concentrated until remaining volume was 120 mL. Co-evaporation with cyclohexane was repeated two times using 120 mL of cyclohexane each time. Final solution (160 mL) was stirred at room temperature. After 30 minutes, solution became cloudy and crystallization started. The slurry was stirred for 2 hours at room temperature and then for 2 hours at 5 to 10° C. Precipitate was filtered off, washed on the filter with cyclohexane (2×30 mL). Since the freezing of cyclohexane causes suction to dry on the filter, wet material was dried under vacuum at 40° C. There was obtained 22 g (69%) of the Compound of Formula (VIa) as a solid and the purity thereof was 98 area % as determined by HPLC (UV detection at 220 nm). Content of the impurity Compound of Formula (VIII) as described herein was 1.2% as determined by HPLC (UV detection at 220 nm).

Example 2

Recrystallization of tert-butyl 3-(2,3-difluorophenyl)-3-hydroxypyrrolidine-1-carboxylate, i.e. the Compound of Formula (VIa)

Crude Compound of Formula (VIa) obtained in Example 1 (21.5 g) was mixed with cyclohexane (130 mL) and the mixture was heated to 60° C. (dissolution started when the internal temperature reached 55° C.). The resulting solution was stirred at 60° C. for 5 min and then cooled to room temperature. Solution became cloudy when the inner temperature reached 41° C. and intensive precipitation started at 36° C. The slurry was stirred at room temperature overnight and then at 10 to 15° C. for 2 hours. Precipitate was filtered off and washed with cyclohexane (2×30 mL). Wet material (freezing of cyclohexane during filtration process under vacuum causes suction to dryness on filter) was charged in the flask and dried under vacuum at 40° C. for 16 hours. There was obtained 19.9 g (93%) of Compound of Formula (VIa) with a purity of 99.8 area-% as determined by HPLC (UV detection at 220 nm). Impurity Compound (VIII) was detected in 0.12% level.

$^1$H NMR (400 MHz, CDCl$_3$): δ 1.47 (s, 9H), 2.2-2.3 (m, 1H), 2.4-2.5 (m, 1H), 2.57 (m, 1H), 3.5-3.9 (m, 4H), 7.1-7.2 (m, 2H), 7.3-7.4 (m, 1H). MS (APCI$^+$) m/z 300 [M+1]$^+$.

Example 3

Synthesis of tert-butyl 3-(2,3-difluorophenyl)-3-methoxypyrrolidine-1-carboxylate, i.e. the Compound of Formula (VIIa)

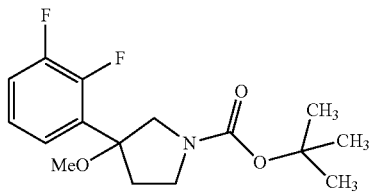

Formula VIIa

THF (120 mL) was charged to a 3-neck round bottom flask followed by Compound of Formula VIa from Example 2. (19.8 g, 66.1 mmol). To the solution was added KOtBu (9.66 g, 85.9 mmol). The mixture was stirred at room temperature for 10 min, then heated to 31° C. (internal temperature) and stirred for 3 hours at 30 to 31° C. Methyl iodide (6.2 mL, 99 mmol) was added keeping the internal temperature below 37° C. (addition time was 10 min). The reaction mixture was stirred at 31° C. for 18 hours. Additional amount of KOtBu (0.6 g, 5 mmol) was added to the reaction mixture in one portion. After one hour, the reaction mixture was cooled to room temperature and diluted with water (300 mL). i-PrOAc (200 mL) was added and layers were separated. The aqueous layer was re-extracted with i-PrOAc (100 mL). The organic layers were combined and washed with brine (180 mL) and then with water (100 mL). The organic layer was concentrated under reduced pressure until the remaining total volume was 200 mL. i-PrOAc (200 mL) was added and distillation continued until 200 mL was left. 200 mL of i-PrOAc was added again and solvent distilled off until remaining volume was approximately 220 mL. Yield of Compound of Formula (VIIa): 97% (determined using aliquot evaporation method) and the purity was 98 area-% as determined by HPLC. The product was used in the next step without isolation.

$^1$H NMR (400 MHz, CDCl$_3$): δ 1.49 (s, 9H), 2.1-2.3 (m, 1H), 2.5-2.6 (m, 1H), 3.07, (s, 3H), 3.5-3.7 (m, 3H), 4.0-4.2 (m, 1H), 7.1-7.2 (m, 3H). MS (APCI$^+$) m/z 314 [M+1]$^+$.

Example 4

Synthesis of racemic 3-(2,3-difluorophenyl)-3-methoxypyrrolidine, i.e. the Compound of Formula (I)

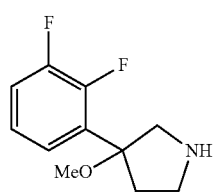

Formula I

The i-PrOAc solution (220 mL) of Compound (VIIa) (calculated, 20.0 g, 63.7 mmol) obtained in Example 3 was cooled to 15° C. and then hydrochloric acid (37%, 26.6 mL, 318 mmol) was added. The cooling bath was removed and the reaction mixture was stirred at room temperature for three hours. The mixture was cooled to 10° C. and water (100 mL) was added. The cooling bath was removed and the mixture stirred at room temperature for one hour. The layers were separated and the organic phase was re-extracted with water (60 mL). The combined aqueous phases were cooled to 0° C. and 50% NaOH aqueous solution was added until a pH of 12.9 was obtained (approximately 50 mL). The cooling bath was removed and the basic aqueous phase was extracted twice with MTBE (120 mL and 60 mL). The combined organic layers were washed with water (60 mL) and then concentrated under reduced pressure until approximately 100 mL were left. Ethanol (100 mL) was added and distillation continued until approximately 100 mL were left. The addition and evaporation procedure with ethanol was repeated twice by adding 100 mL of fresh ethanol each time. Final distillation continued until the remaining volume approximately was 22 mL.

Yield of Compound of Formula (I): 79% (determined using aliquot evaporation method) and the purity was 98 area-% as determined by HPLC. The product was used in the next step without isolation.

$^1$H NMR (400 MHz, CDCl$_3$): δ 2.00 (m, 2H), 2.1-2.2 (m, 1H), 2.4-2.5 (m, 1H), 2.9-3.1, (m, 5H), 3.2-3.3 (m, 1H), 3.5-3.6 (m, 1H), 7.0-7.2 (m, 3H). MS (APCI$^+$) m/z 214 [M+1]$^+$.

Example 5

Synthesis of (−)-dibenzoyl-L-tartaric acid salt of (+)-3-(2,3-difluorophenyl)-3-methoxypyrrolidine. i.e. the Salt of Formula (IIa)

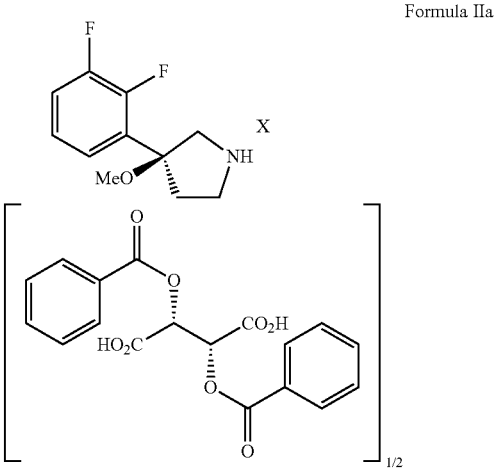

Formula IIa (−)-Dibenzoyl-L-tartaric acid (5.08 g, 14.2 mmol) was dissolved in ethanol (99%, contains 1% of methyl ethyl ketone) (46 mL) and the solution was heated to 55° C. An ethanol solution of Compound (I) (22 mL from Example 4, calculated to be 10.8 g, 50.7 mmol) was added to the acid solution. The flask was rinsed with ethanol (2 mL) and added to the reaction mixture. The reaction mixture was stirred at 55° C. for 5 min., then cooled to room temperature and left overnight at room temperature under stirring. The slurry was stirred at 0 to 5° C. for 3 hours. The precipitate was filtered and the filter cake was washed with ethanol (2×20 mL).

Product was dried on air and there was obtained 7.0 g (63% based on a theoretical yield of 11.1 g) of salt of Formula (IIa) with a purity of 99.7 area-% (HPLC). The ratio of the two stereo isomers was 98.8:1.2.

$^1$H NMR (400 MHz, DMSO-$d_6$): δ 1.9-2.1 (m, 1H), 2.5-2.6 (m, 1H), 2.86 (s, 3H), 3.0-3.2 (m, 3H), 3.6-3.7 (m, 1H), 5.57 (s, 1H), 7.1-7.3 (m, 2H), 7.4-7.5 (m, 3H), 7.6-7.7 (m, 1H), 7.94 (d, 2H). The NMR spectrum above showed that the ratio between the Compound of Formula II and (−)-dibenzoyl-L-tartaric acid was 2:1.

The absolute configuration was determined for a combination of the compound of Formula II and (−)-dibenzoyl-L-tartaric acid in a 1:1 ratio (i.e. the salt of Formula IIa'), which was synthesized in a similar manner as in Example 5, from single X-ray diffraction. By comparing the chirality (R, R) of the tartaric acid in the obtained model, it was confirmed that the absolute configuration of the crystallographic model was correct and that Compound of Formula II is an S form.

Example 6

Synthesis of (+)-3-(2,3-difluorophenyl)-3-methoxypyrrolidine, i.e. the Compound of Formula (II)

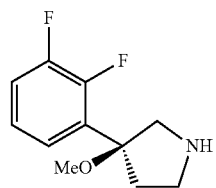

Formula II

In a flask, K$_2$CO$_3$ (4.77 g, 34.5 mmol) was dissolved in water (25 mL). To the prepared solution, DCM (65 mL) and salt of Formula (IIa) (6.77 g, 17.3 mmol) were added. The mixture was stirred at room temperature for 20 min. Layers were separated and the aqueous phase was re-extracted with DCM (30 mL). The combined organic extracts were washed with water (3×20 mL). The organic layer was concentrated under reduced pressure and co-evaporated three times with ethanol (3×30 mL) affording 3.25 g (89% yield) of Compound of Formula (II).

Example 7

Synthesis of fumarate Salt of (+)-3-(2,3-difluorophenyl)-3-methoxypyrrolidine, i.e. the Salt of Formula IIb

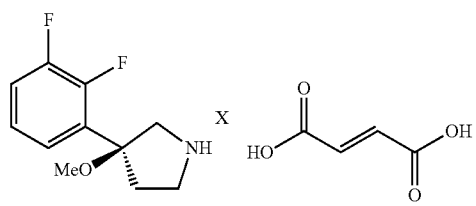

Formula IIb

Fumaric acid (1.77 g, 15.2 mmol) was dissolved in ethanol (99%, contains 1% of methyl ethyl ketone) (54 mL) at room temperature. The solution of Compound (II) from Example 6 (3.25 g, 15.2 mmol) in ethanol (6 mL) was added to the acid solution. The flask was rinsed with ethanol (2.8 mL) and added to the reaction mixture. The reaction mixture was stirred at room temperature overnight and then at 0 to 5° C. for 2 hours. The precipitate was filtered and the filter cake was washed with ethanol (2×15 mL). There was obtained 4.22 g (84% yield) of fumarate salt of Formula IIb with a purity of 100 area-% (HPLC). The ratio of the two enantiomers was 99.5:0.5 (i.e. 99% e.e.). Purity according to a $^1$H-NMR assay was 99.5%.

$^1$H NMR (400 MHz, DMSO-$d_6$): δ 2.1-2.2 (m, 1H), 2.6-2.7 (m, 1H), 2.94 (s, 3H), 3.1-3.4 (m, 3H), 3.7-3.8 (m, 2H), 6.44 (s, 1H), 7.2-7.3 (m, 2H), 7.4-7.5 (m, 1H).

X-ray powder diffraction analysis was performed on a sample of the crystals of the fumarate salt of (+)-3-(2,3-difluorophenyl)-3-methoxypyrrolidine as prepared above according to standard methods using the instrument, equipment and the conditions described in the general description. The analysis provided the diffractogram depicted in FIG. 1. The main characteristic peaks, with positions and relative intensities, have been extracted from the diffractogram in FIG. 1 and is given below in Table 1.

It will be understood that the relative intensities of peaks may vary according to the orientation of the sample under test and on the type and setting of the instrument used so that the intensities in the XRD traces included herein are illustrative and not intended to be used for absolute comparison.

TABLE 1

Table 1: Positions and intensities of the major peaks in the XRP-diffractogram of the salt of Formula IIb.

| Angle 2θ/° | d-value/Å | % Relative intensity |
|---|---|---|
| 6.66 | 13.25 | 43 |
| 10.03 | 8.82 | 6 |
| 12.30 | 7.19 | 23 |
| 13.41 | 6.60 | 96 |
| 14.00 | 6.32 | 7 |
| 14.52 | 6.10 | 12 |
| 15.56 | 5.69 | 7 |
| 16.27 | 5.44 | 30 |
| 16.42 | 5.39 | 22 |
| 16.69 | 5.31 | 18 |
| 17.11 | 5.18 | 7 |
| 17.53 | 5.06 | 27 |
| 18.40 | 4.82 | 23 |
| 18.85 | 4.70 | 11 |
| 19.25 | 4.61 | 16 |
| 20.61 | 4.31 | 10 |
| 21.22 | 4.18 | 3 |
| 21.69 | 4.09 | 21 |
| 23.35 | 3.98 | 19 |
| 23.16 | 3.84 | 100 |
| 23.55 | 3.78 | 14 |
| 23.89 | 3.72 | 6 |
| 24.74 | 3.60 | 13 |
| 26.07 | 3.42 | 4 |
| 27.05 | 3.29 | 11 |
| 27.79 | 3.21 | 42 |
| 28.22 | 3.16 | 5 |
| 29.38 | 3.04 | 47 |
| 31.00 | 2.88 | 12 |
| 31.24 | 2.86 | 14 |
| 32.83 | 2.73 | 9 |
| 34.02 | 2.63 | 34 |

Examples 8-16: General Procedure for the Synthesis of Various Acid Addition Salts of (+)-3-(2,3-difluorophenyl)-3-methoxypyrrolidine The acid (2 mmol) was added to (+)-3-(2,3-difluorophenyl)-3-methoxypyrrolidine (2 mmol) in ethanol (3 mL) and if needed the mixture was heated to reflux until full dissolution, then cooled to room temperature. If precipitation occurred, the resultant solid was collected by filtration and dried in vacuo at 40° C. overnight. If precipitation did not occur in ethanol, the solution was cooled to −18° C. and/or treated with various solvents until precipitation occurred, or evaporated and the resultant residue was treated with alternative solvents until precipitation occurred. The base/acid ratio of the obtained salts was determined by $^1$H NMR spectroscopy with a relaxation time of at least 10 seconds or by elemental analysis. Melting point was determined by DSC (Differential scanning calorimetry) and the solid-state characterization was determined by XRPD, which was used to determine if the precipitated salt was crystalline.

Example 8

Hydrochloric Acid Salt of (+)-3-(2,3-difluorophenyl)-3-methoxypyrrolidine

The title salt was prepared according to the general procedure above, and precipitated when MTBE was added to an ethanol solution of the acid and the base. The salt was crystalline but the crystallization did not seem to have a purification effect.
Yield: 59%.
Base/acid ratio: 1:1.
Melting point: 196.9° C.
Solubility in water: 213 mg/mL.

Example 9

L-Tartaric acid salt of (+)-3-(2,3-difluorophenyl)-3-methoxypyrrolidine

The title salt was prepared according to the general procedure above, and precipitated from an ethanol solution. The salt was crystalline.
Yield: 91%.
Base/acid ratio: 1:1.
Melting point: 185.4° C.
Solubility in water: 53 mg/mL.

Example 10

Succinic Acid Salt of (+)-3-(2,3-difluorophenyl)-3-methoxypyrrolidine

The title salt was prepared according to the general procedure above, and precipitated when ethyl acetate was added to an isopropanol solution of the acid and the base. The salt was crystalline.
Yield: 83%.
Base/acid ratio: 1:1.
Melting point: 105.1° C.
Solubility in water: 159 mg/mL.

Example 11

Fumaric Acid Salt of (+)-3-(2,3-difluorophenyl)-3-methoxypyrrolidine

The title salt was prepared according to the general procedure above, and precipitated from an ethanol solution. The salt was crystalline.
Yield: 79%.
Base/acid ratio: 1:1.
Melting point: 164.1° C.
Solubility in water: 34 mg/mL. The value for water solubility of the fumaric acid salt was found to be 74.1 mg/mL when measured by the Flask method water solubility test.

Example 12

Maleic Acid Salt of (+)-3-(2,3-difluorophenyl)-3-methoxypyrrolidine

The title salt was prepared according to the general procedure above, and precipitated from an ethyl acetate solution of the acid and the base. The salt was crystalline.
Yield: 74%.
Base/acid ratio: 1:0.8.
Melting point: 93.5° C.
Solubility in water: 161 mg/mL.

Example 13

L-Malic Acid Salt of (+)-3-(2,3-difluorophenyl)-3-methoxypyrrolidine

The title salt was prepared according to the general procedure above, and precipitated from an isopropanol solution of the acid and the base. The salt was crystalline.
Yield: 88%.
Base/acid ratio: 1:1.
Melting point: 123.8° C.
Solubility in water: 132 mg/mL.

Example 14

Citric Acid Salt of (+)-3-(2,3-difluorophenyl)-3-methoxypyrrolidine

The title salt was prepared according to the general procedure above, and precipitated from a diluted isopropanol solution of the acid and the base.
XRPD and DSC analyses were not recorded due to large amount of residual solvent in the sample.
Yield: 81%.
Base/acid ratio: 1:1.

Example 15

Sulfuric Acid Salt of (+)-3-(2,3-difluorophenyl)-3-methoxypyrrolidine

The title salt was prepared according to the general procedure above, and precipitated when MTBE was added to an acetonitrile solution of the acid and the base. The salt was crystalline.
Yield: 80%.
Base/acid ratio: 1:1.
Melting point: 128.7° C.
Solubility in water: 167 mg/mL.

Example 16

Hydrobromic Acid Salt of (+)-3-(2,3-difluorophenyl)-3-methoxypyrrolidine

The title salt was prepared according to the general procedure above, and precipitated when methanol was added to an MTBE solution of the acid and the base. The salt was crystalline.
Yield: 82%.
Base/acid ratio was not determined.
Melting point: 154.8° C.
Solubility in water: 401 mg/mL.

Example 17: Hygroscopicity Test of Acid Addition Salts of (+)-3-(2,3-difluorophenyl)-3-methoxypyrrolidine After each salt obtained in Examples 8 to 16 was characterized, four of them (hydrochloride, Example 8; tartrate, Example 9; fumarate, Example 11; and L-malate, Example 13) were eventually tested in a hygroscopicity test as described herein. In the followed hygroscopicity test, the change in weight was measured after each acidic salt of (+)-3-(2,3-difluorophenyl)-3-methoxypyrrolidine was exposed for a week under the condition of 30° C. and different relative humidities (RH) 0 to 97%. The results are shown in Table 2.

TABLE 2

Hygroscopicity determination of four acid addition salts according to Example 8, Example 9, Example 11 and Example 13.

| Relative Humidity (%) | Weight difference (%) Example 8 | Weight difference (%) Example 9 | Weight difference (%) Example 11 | Weight difference (%) Example 13 |
|---|---|---|---|---|
| 0 | 0.00 | −2.36 | −0.07 | −0.07 |
| 6 | −0.07 | −0.67 | −0.14 | 0.00 |
| 11 | −0.06 | −0.14 | 0.11 | −0.13 |
| 22 | −0.15 | 2.40 | 0.15 | −0.08 |
| 32 | 0.00 | 2.16 | 0.13 | 0.00 |
| 43 | −0.13 | 1.71 | 0.07 | −0.22 |
| 56 | −0.14 | 1.99 | 0.19 | −0.06 |
| 73 | −0.13 | 1.90 | 0.06 | 0.07 |
| 84 | 25.77 | 2.13 | 0.00 | 0.40 |
| 97 | 99.12 | 2.39 | 0.16 | 34.37 |

As shown in Table 2, the fumaric acid salt of (+)-3-(2,3-difluorophenyl)-3-methoxypyrrolidine according to Example 11 does not adsorb or desorb water at any humidity. Thus, the salt has a very low hygroscopicity, i.e. a weight change of ±0.2% or less, even when it is exposed to a very high relative humidity such as 73%, 83% or 97% for a week at 30° C. These properties, together with a high solubility in water, a high crystallinity and a high melting point, show that the fumaric acid addition salt has excellent pharmaceutical properties.

Example 18: In Vitro Binding Assay and Data, Human Sigma 1 Receptor

The binding affinity of the fumaric acid salt of (+)-3-(2,3-difluorophenyl)-3-methoxypyrrolidine at the human sigma 1 receptor was determined by a competition binding assay similar to what is described in GANAPATHY, M. E., PRASAD, P. D., HUANG, W., SETH, P., LEIBACH, F. H. and GANAPATHY, V. (1999), Molecular and ligand-binding characterization of the σ-receptor in the Jurkat human T lymphocyte cell line, J. Pharmacol. Exp. Ther., 289: 251.

Cell membrane homogenates (150 μg protein) were incubated for 120 min at 37° C. with 15 nM [$^3$H] pentazocine in the absence or presence of the test compound in a buffer containing 50 mM Tris-HCl (pH 8).

Nonspecific binding was determined in the presence of 10 μM haloperidol.

Following incubation, the samples were filtered under vacuum through glass fiber filters (GF/B, Packard) pre-soaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard).

The results were expressed as a percent inhibition of the control radioligand specific binding.

The standard reference compound was haloperidol, which was tested in each experiment at several concentrations to obtain a competition curve from which its IC50 value was calculated.

The test compound was tested in a single concentration at 1.0 E-5 M and in duplicate.

The reported value in Table 3 is a mean value.

TABLE 3

Percent inhibition from radioligand binding assay.

| Example | Human Sigma 1 receptor |
|---|---|
| 7 | 79.1% |

Reference Example 19 (Reference Compound Disclosed in WO 2010/058018)

Synthesis of oxalic Acid Salt of (+)-3-(2,3-difluorophenyl)-3-methoxypyrrolidine Oxalic acid (6.9 g, 54.7 mmol) was added to a solution of (+)-3-(2,3-difluorophenyl)-3-methoxypyrrolidine (12.0 g, 56.3 mmol) in methanol (200 mL). The mixture was heated to 50° C. for 5 minutes and then allowed to reach room temperature. Diethyl ether (100 mL) was slowly added to the resultant precipitate and the mixture was stirred at 0° C. for 2 hours. The product was isolated by filtration and the solid was washed with diethyl ether. After drying in the hood overnight, the product was dried further in an oven at 70° C. for 2 h. There was obtained 15.6 g of the title compound as a crystalline product. $^1$H NMR (800 MHz, DMSO-$d_6$): δ 2.23 (m, 1H), 2.76 (m, 1H), 2.95 (s, 3H), 3.27 (m, 1H), 3.42 (m, 2H), 3.87 (m, 1H), 7.30 (m, 2H), 7.52 (m, 1H).
Yield: 91%.
Base/acid ratio according to elemental analysis: 1:1.
Melting point: 185.1° C.
Solubility in water (Flask method water solubility test): 28 mg/mL.

The oxalic acid salt of (+)-3-(2,3-difluorophenyl)-3-methoxypyrrolidine was subjected to the hygroscopicity test described herein. The result is shown below in Table 4.

TABLE 4

Hygroscopicity determination of the oxalic acid salt according to Reference Example 19.

| Relative Humidity (%) | Weight difference (%) Reference Example 19 |
|---|---|
| 0 | 0.00 |
| 6 | 0.00 |
| 11 | −0.21 |
| 22 | 0.00 |
| 32 | 0.11 |
| 43 | −0.05 |
| 56 | 0.00 |
| 73 | −0.05 |
| 84 | −0.15 |
| 97 | 0.26 |

Remarks

As shown hereinabove, the fumaric acid salt of (+)-3-(2,3-difluorophenyl)-3-methoxypyrrolidine according to Example 11 has a solubility in water (74.1 mg/mL) that is about two-and-a-half fold higher than the aqueous solubility of the corresponding oxalic acid salt according to Reference Example 19 (28 mg/mL). Since drug dissolution is the rate-limiting step to absorption from the gastro-intestinal tract, the salt of Formula IIb possesses significantly enhanced pharmaceutical properties as compared to the Reference compound. Thus, the fumaric acid salt of (+)-3-(2,3-difluorophenyl)-3-methoxypyrrolidine according to Example 11 has both satisfactory water solubility and hygroscopicity. Additionally, it has a melting point of 164.1° C. making it suitable for manufacturing of a pharmaceutical composition such as a tablet.

REFERENCES

1. WO 2010/0580182.
2. J. Pharmacol. Exp. Ther., 1999, 289: 251.
3. EP 1 582 524 A1

The invention claimed is:

1. A process for manufacturing the salt of Formula IIb

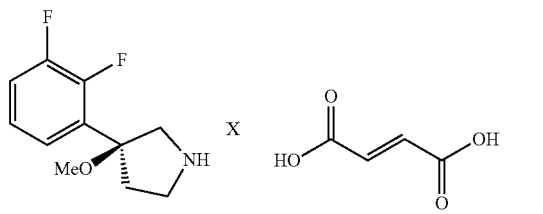

Formula IIb said process comprising:
resolution of a compound of Formula I:

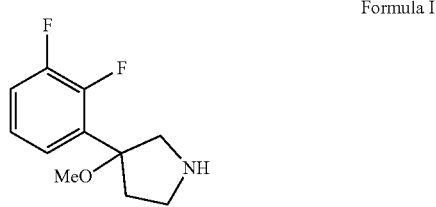 [SMILES: COC1(c2cccc(F)c2F)CCNC1]

Formula I by combining said compound of Formula I with (−)-dibenzoyl-L-tartaric acid in the presence of at least one solvent thereby providing a salt of Formula IIa:

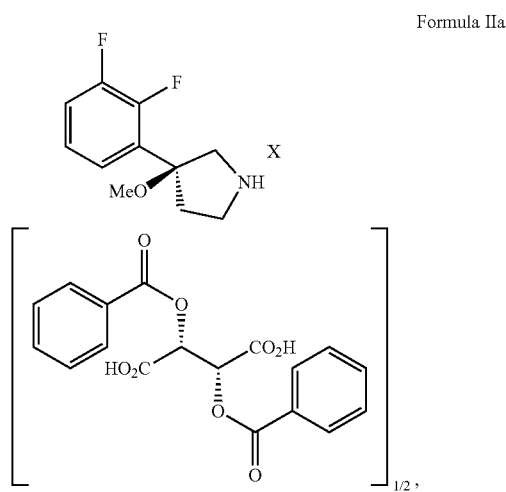

Formula IIa optionally isolating and drying the salt of Formula IIa,
removing the (−)-dibenzoyl-L-tartaric acid from the salt of Formula IIa thereby providing a compound of Formula II,

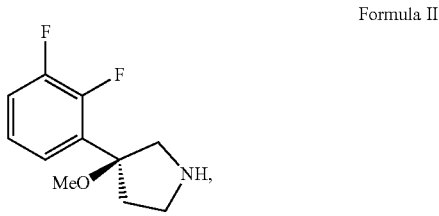 [SMILES: CO[C@]1(c2cccc(F)c2F)CCNC1]

Formula II and
combining the compound of Formula II with fumaric acid thereby providing the salt of Formula IIb.

2. The process according to claim 1, wherein the (−)-dibenzoyl-L-tartaric acid is removed from the salt of Formula IIa by treating the salt of Formula IIa with a base thereby providing the compound of Formula II.

3. The process according to claim 1, wherein the resolution comprises:
  a) dissolving the (−)-dibenzoyl-L-tartaric acid in the at least one solvent, optionally by heating, to provide a first solution,
  b) adding a solution comprising the compound of Formula I and at least one further solvent to said first solution thereby providing a second solution, and
  c) precipitating the salt of Formula IIa, optionally by cooling, from said second solution.

4. The process according to claim 1, wherein the at least one solvent comprises methanol, ethanol, 1-propanol, 2-propanol, 1-butanol, or 2-butanol, and any combination thereof.

5. The process according to claim 1, wherein the at least one solvent comprises ethanol.

6. The process according to claim 2, wherein said treatment with the base comprises the steps of:
mixing the salt of Formula IIa with a mixture of a first water-insoluble solvent and an aqueous solution comprising a base, thereby forming:

(i) a solvent phase comprising the first water-insoluble solvent, and
(ii) an aqueous phase comprising the aqueous solution comprising the base,
extracting (ii) with a second water-insoluble solvent to provide:
(iii) at least one phase comprising the second water-insoluble solvent,
combining the phases (i) and (iii),
evaporating the first and second water-insoluble solvents from the combined phases (i) and (iii) thereby providing the compound of Formula II.

7. The process according to claim 6, wherein:
the base comprises potassium carbonate, and/or
the first water-insoluble solvent and/or the second water-insoluble solvent comprise(s) dichloromethane.

8. The process according to claim 1, wherein the molar ratio between the compound of Formula I and the (−)-dibenzoyl-L-tartaric acid is within the range of from about 1.9:1 to about 2.1:1.

9. The process according to claim 1, wherein the salt of Formula IIb is precipitated from an ethanol solution comprising the compound of Formula II and fumaric acid in a 1:1 ratio.

10. The process according to claim 1, wherein the compound of Formula I is prepared using a method comprising the steps of:
reacting a compound of Formula IV with a compound of Formula V to provide a compound of Formula VI:

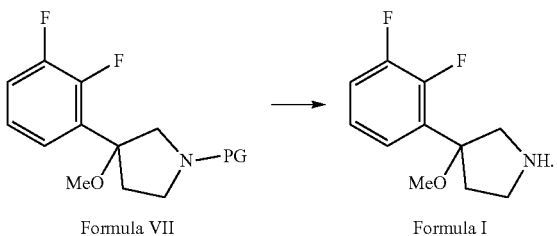

wherein:
"M" represents an alkali metal or an alkaline earth metal halide,
PG represents a protecting group,
subjecting the compound of Formula VI to recrystallization from at least one solvent comprising cyclohexane,
converting the compound of Formula VI into the compound of Formula VII:

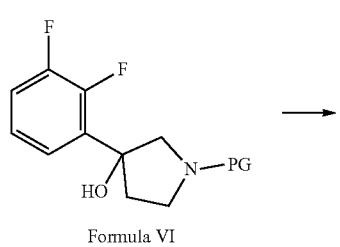

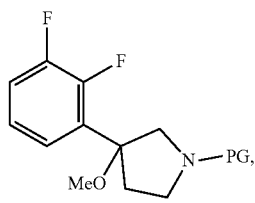

and
removing the protecting group from the compound of Formula VII thereby providing the compound of Formula I:

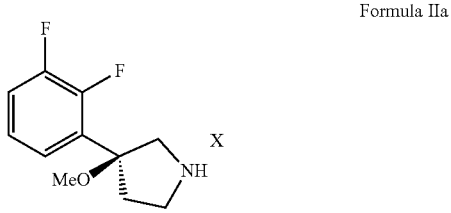

11. A salt of Formula IIa:

12. The process according to claim 10, wherein the protecting group is tert-butoxycarbonyl.

13. The process according to claim 3, wherein the at least one further solvent comprises methanol, ethanol, 1-propanol, 2-propanol, 1-butanol, or 2-butanol, and any combination thereof.

14. The process according to claim 13, wherein the at least one further solvent comprises ethanol.

* * * * *

UNITED STATES PATENT AND TRADEMARK OFFICE
CERTIFICATE OF CORRECTION

PATENT NO. : 11,078,158 B2
APPLICATION NO. : 16/338055
DATED : August 3, 2021
INVENTOR(S) : Sonessen et al.

Page 1 of 1

It is certified that error appears in the above-identified patent and that said Letters Patent is hereby corrected as shown below:

In the Specification

In Column 7, Line 57 please replace "Iatrogenic" with "iatrogenic"

In Column 9, Line 36 please replace "a a" with "a"

In Column 18, Line 6 please replace "Formula IIa" with "Formula IIa'"

In Column 22, Line 4 please replace heading "Salts" with "Salts"

In Column 22, Line 55 please replace heading "Isotopes" with "Isotopes"

In Column 24, Line 16 please replace heading "Hygroscopicity Test" with "Hygroscopicity Test"

In Column 24, Line 22 please replace heading "Regular Water Solubility Test" with "Regular Water Solubility Test"

In Column 24, Line 48 please replace heading "Flask Method Water Solubility Test" with "Flask Method Water Solubility Test"

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*